(12) United States Patent
Van Pijkeren et al.

(10) Patent No.: US 10,376,563 B1
(45) Date of Patent: Aug. 13, 2019

(54) METHODS FOR SYSTEMICALLY DELIVERING POLYPEPTIDES AND MICROORGANISMS THEREFOR

(71) Applicant: WISCONSIN ALUMNI RESEARCH FOUNDATION, Madison, WI (US)

(72) Inventors: Jan Peter Van Pijkeren, Madison, WI (US); Alan Attie, Madison, WI (US); Mark Keller, McFarland, WI (US); Jee-Hwan Oh, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 15/431,373

(22) Filed: Feb. 13, 2017

Related U.S. Application Data

(60) Provisional application No. 62/294,578, filed on Feb. 12, 2016.

(51) Int. Cl.

| | |
|---|---|
| *C12N 15/74* | (2006.01) |
| *A61K 35/74* | (2015.01) |
| *A61K 38/00* | (2006.01) |
| *A61K 39/09* | (2006.01) |
| *A61K 38/20* | (2006.01) |
| *A61K 35/747* | (2015.01) |
| *A61K 38/02* | (2006.01) |
| *A61K 9/00* | (2006.01) |
| *C07K 14/54* | (2006.01) |
| *A61K 35/00* | (2006.01) |

(52) U.S. Cl.
CPC ............ *A61K 38/20* (2013.01); *A61K 9/0053* (2013.01); *A61K 35/747* (2013.01); *A61K 38/02* (2013.01); *C07K 14/54* (2013.01); *A61K 2035/11* (2013.01)

(58) Field of Classification Search
CPC ...... C12N 15/74; C12N 15/746; A61K 35/74; A61K 38/00; A61K 39/09
See application file for complete search history.

(56) References Cited

U.S. PATENT DOCUMENTS

| | | | |
|---|---|---|---|
| 7,344,867 B2 | 3/2008 | Connolly | |
| 9,103,831 B2 | 8/2015 | O'Sullivan et al. | |
| 2012/0189550 A1* | 7/2012 | O'Sullivan | A61K 35/74 424/9.6 |

OTHER PUBLICATIONS

McGee et al., IL-22 Promotes Fibroblast-Mediated Wound Repair in the Skin Journal of Investigative Dermatology (2013) 133, 1321-1329.*
Ahrné, S., Molin, G., & Axelsson, L.; Transformation of *Lactobacillus reuteri* with electroporation: Studies on the erythromycin resistance plasmid pLUL631; *Current Microbiology* (1992), 24: 199-205.
Alvarez-Sieiro P, Montalbán-López M, Mu D, Kuipers OP; Bacteriocins of lactic acid bacteria: extending the family. *Appl Microbiol Biotechnol*. 2016. 100(7):2939-51.
Bahey-El-Din, Mohammed, Cormac GM Gahan, and Brendan T. Griffin.; Lactococcus lactis as a cell factory for delivery of therapeutic proteins.; *Current gene therapy* 10.1 (2010): 34-45.
Barrangou, Rodolphe, and Jan-Peter van Pijkeren. "Exploiting CRISPR—Cas immune systems for genome editing in bacteria." *Current opinion in biotechnology* 37 (2016): 61-68.
Becker, Stephen C., et al. "LysK CHAP endopeptidase domain is required for lysis of live staphylococcal cells." *FEMS microbiology letters* 294.1 (2009): 52-60.
Beisel, Chase L., Ahmed A. Gomaa, and Rodolphe Barrangou. "A CRISPR design for next-generation antimicrobials." *Genome biology* 15.11 (2014): 516.
Bikard, David, et al. "Exploiting CRISPR—Cas nucleases to produce sequence-specific antimicrobials." *Nature biotechnology* 32.11 (2014): 1146-1150.
Borysowski, Jan, Beata Weber-Dąbrowska, and Andrzej Górski. "Bacteriophage endolysins as a novel class of antibacterial agents." *Experimental Biology and Medicine* 231.4 (2006): 366-377.
Bourguet, Feliza A., et al. "Characterization of a novel lytic protein encoded by the Bacillus cereus E33L gene ampD as a Bacillus anthracis antimicrobial protein." *Applied and environmental microbiology* 78.8 (2012): 3025-3027.
Britton, Robert A., et al. "Probiotic L. reuteri treatment prevents bone loss in a menopausal ovariectomized mouse model." *Journal of cellular physiology* 229.11 (2014): 1822-1830.
Chatel, J. M., et al. "In vivo transfer of plasmid from food-grade transiting lactococci to murine epithelial cells." *Gene therapy* 15.16 (2008): 1184-1190.
Cheng, Xiaodong, et al. "The structure of bacteriophage T7 lysozyme, a zinc amidase and an inhibitor of T7 RNA polymerase." *Proceedings of the National Academy of Sciences* 91.9 (1994): 4034-4038.
Citorik, Robert J., Mark Mimee, and Timothy K. Lu. "Sequence-specific antimicrobials using efficiently delivered RNA-guided nucleases." *Nature biotechnology* 32.11 (2014): 1141-1145.
Cotter, Paul D., R. Paul Ross, Colin Hill. "Bacteriocins—a viable alternative to antibiotics?." *Nature Reviews Microbiology* 11.2 (2013): 95-105.
Cronin, Michelle, et al. "High resolution in vivo bioluminescent imaging for the study of bacterial tumour targeting." *PloS one* 7.1 (2012): e30940.
Cronin, Michelle, et al. "Orally administered bifidobacteria as vehicles for delivery of agents to systemic tumors." *Molecular Therapy* 18.7 (2010): 1397-1407.

(Continued)

*Primary Examiner* — Maria G Leavitt
(74) *Attorney, Agent, or Firm* — Daniel A. Blasiole; DeWitt LLP

(57) ABSTRACT

Methods and microorganisms for systemically introducing a polypeptide in the bloodstream of a subject. The methods of the invention include administering into the gastrointestinal tract of a subject a bacterium configured to express and produce and release the polypeptide. The bacterium is administered in an amount effective to introduce the polypeptide in the bloodstream of the subject, preferably in a detectable amount. The microorganisms of the invention include lactic acid bacteria, such as *Lactobacillus reuteri*, that comprise a recombinant gene configured to express a polypeptide to be systemically introduced.

11 Claims, 12 Drawing Sheets

Specification includes a Sequence Listing.

(56) References Cited

OTHER PUBLICATIONS

De Azevedo, Marcela, et al. "In vitro and in vivo characterization of DNA delivery using recombinant Lactococcus lactis expressing a mutated form of L. monocytogenes Internalin A." *BMC microbiology* 12.1 (2012): 299.

De Ruyter, P. G., Oscar P. Kuipers, and Willem M. De Vos. "Controlled gene expression systems for Lactococcus lactis with the food-grade inducer nisin." *Applied and environmental microbiology* 62.10 (1996): 3662-3667.

De Weirdt, Rosemarie, et al. "Glycerol supplementation enhances L. reuteri's protective effect against S. Typhimurium colonization in a 3-D model of colonic epithelium." *PLoS One* 7.5 (2012): e37116.

Dishisha, Tarek, et al. "Flux analysis of the Lactobacillus reuteri propanediol-utilization pathway for production of 3-hydroxypropionaldehyde, 3-hydroxypropionic acid and 1, 3-propanediol from glycerol." *Microbial cell factories* 13.1 (2014): 76.

Doleyres, Y., et al. "Production of 3-hydroxypropionaldehyde using a two-step process with Lactobacillus reuteri." *Applied microbiology and biotechnology* 68.4 (2005): 467-474.

Eaton, Kathryn A., et al. "Probiotic Lactobacillus reuteri ameliorates disease due to enterohemorrhagic Escherichia coli in germfree mice." *Infection and immunity* 79.1 (2011): 185-191.

Elzagheid, Adam, et al, "E-cadherin expression pattern in primary colorectal carcinomas and their metastases reflects disease outcome." *World journal of gastroenterology: WJG* 12.27 (2006): 4304.

Field, Des, et al. "Bioengineered nisin A derivatives with enhanced activity against both Gram positive and Gram negative pathogens." *PLoS One* 7.10 (2012): e46884.

Field, Des, et al. "The generation of nisin variants with enhanced activity against specific gram-positive pathogens." *Molecular microbiology* 69.1 (2008): 218-230.

Fischetti, Vincent A. "12 The Use of Phage Lytic Enzymes to Control Bacterial Infections." *Bacteriophages: Biology and applications* (2004): 321.

Fischetti, Vincent A. "Bacteriophage Lysins: the Ultimate Enzybiotic." *Enzybiotics: Antibiotic Enzymes as Drugs and Therapeutics* (2010): 107-122.

Fogel, M. R., and Gary M. Gray. "Starch hydrolysis in man: an intraluminal process not requiring membrane digestion." *Journal of applied physiology* 35.2 (1973): 263-267.

Foster, Patricia L. "Methods for determining spontaneous mutation rates." *Methods in enzymology* 409 (2006): 195-213.

Frese, Steven A., et al. "The evolution of host specialization in the vertebrate gut symbiont Lactobacillus reuteri." *PLoS genetics* 7.2 (2011): e1001314.

Fu, Geng-Feng, et al. "Bifidobacterium longum as an oral delivery system of endostatin for gene therapy on solid liver cancer." *Cancer gene therapy* 12.2 (2005): 133-140.

Gibson, Daniel G., et al. "Enzymatic assembly of DNA molecules up to several hundred kilobases." *Nature methods* 6.5 (2009): 343-345.

Gomaa, Ahmed A., et al. "Programmable removal of bacterial strains by use of genome-targeting CRISPR—Cas systems." *MBio* 5.1 (2014): e00928-13.

Green et al., Molecular Cloning: A Laboratory Manual, 4th ed., Cold Spring Harbor Laboratory Press, 2012.

Guimarães, Valeria Dellaretti, et al. "Internalin-expressing Lactococcus lactis is able to invade small intestine of guinea pigs and deliver DNA into mammalian epithelial cells." *Microbes and infection* 7.5 (2005): 836-844.

Guimarães, Valeria, et al. "A new plasmid vector for DNA delivery using lactococci." *Genetic vaccines and therapy* 7.1 (2009): 4.

Hill, C., Guarner, F., Reid, G., Gibson, G.R., Merenstein, D.J., Pot, B., Morelli, L., Canani, R.B., Flint, H.J., Salminen, S. and Calder, P.C. (2014). Expert consensus document: The International Scientific Association for Probiotics and Prebiotics consensus statement on the scope and appropriate use of the term probiotic. *Nature reviews Gastroenterology & hepatology*, 11(8),506-514.

Huyghebaert, Nathalie, et al. "Development of an enteric-coated formulation containing freeze-dried, viable recombinant Lactococcus lactis for the ileal mucosal delivery of human interleukin-10." *European Journal of Pharmaceutics and Biopharmaceutics* 60.3 (2005): 349-359.

Jacobs, C., et al. "Bacterial cell wall recycling provides cytosolic muropeptides as effectors for beta-lactamase induction." *The EMBO journal* 13.19 (1994): 4684.

Jacobs, Christine, et al. "AmpD, essential for both β-lactamase regulation and cell wall recycling, is a novel cytosolic N-acetylmuramyl-L-alanine amidase." *Molecular microbiology* 15.3 (1995): 553-559.

Jensen, Hanne, et al. "Role of Lactobacillus reuteri cell and mucus-binding protein A (CmbA) in adhesion to intestinal epithelial cells and mucus in vitro." *Microbiology* 160.4 (2014): 671-681.

Kok, Stefan de, et al. "Rapid and reliable DNA assembly via ligase cycling reaction." *ACS synthetic biology* 3.2 (2014): 97-106.

Kommineni, Sushma, et al. "Bacteriocin production augments niche competition by enterococci in the mammalian gastrointestinal tract." *Nature* 526.7575 (2015): 719-722.

Lecuit, M. A. R. C., et al. "Internalin of Listeria monocytogenes with an intact leucine-rich repeat region is sufficient to promote internalization." *Infection and immunity* 65.12 (1997): 5309-5319.

Li, C., Chen, X., Kou, L., Hu, B., Zhu, L., Fan, Y. . . . Xu, G. (2010); Selenium-Bifidobacterium longum as a delivery system of endostatin for inhibition of pathogenic bacteria and selective regression of solid tumor; *Experimental and Therapeutic Medicine*, 1, 129-135.

Liu, Yuying, et al. "Human-derived probiotic Lactobacillus reuteri strains differentially reduce intestinal inflammation." *American Journal of Physiology-Gastrointestinal and Liver Physiology* 299.5 (2010): G1087-G1096.

Loessner, Martin J. "Bacteriophage endolysins—current state research and applications." *Current opinion in microbiology* 8.4 (2005): 480-487.

Loessner, Martin J., et al. "C-terminal domains of Listeria monocytogenes bacteriophage murein hydrolases determine specific recognition and high-affinity binding to bacterial cell wall carbohydrates." *Molecular microbiology* 44.2 (2002): 335-349.

Loonen, L. MP, et al. "REG3γ-deficient mice have altered mucus distribution and increased mucosal inflammatory responses to the microbiota and enteric pathogens in the ileum." *Mucosal immunology* 7.4 (2014): 939-947.

Loonen, Linda MP. *RegIII proteins as gatekeepers of the intestinal epithelium*. 2013 Thesis, Wageningen University, 2013. 208 pages.

López, Rubens, et al. "The pneumococcal cell wall degrading enzymes: a modular design to create new lysins?." *Microbial Drug Resistance* 3.2 (1997): 199-211.

MacKenzie, Donald A., et al. "Strain-specific diversity of mucus-binding proteins in the adhesion and aggregation properties of Lactobacillus reuteri." *Microbiology* 156.11 (2010): 3368-3378.

Navarre, William Wiley, et al. "Multiple Enzymatic Activities of the Murein Hydrolase from Staphylococcal Phage φ11 Identification of a d-Alanyl-Glycine Endopeptidase Activity." *Journal of Biological Chemistry* 274.22 (1999): 15847-15856.

Nelson, Daniel, et al. "PlyC: a multimeric bacteriophage lysin." *Proceedings of the National Academy of Sciences* 103.28 (2006): 10765-10770.

Nicoletti, Mauro, and Giuseppe Elertani. "DNA fusion product of phage P2 with plasmid pBR1022: a new phasmid." *Molecular and General Genetics MGG* 189.2 (1983): 343-347.

Oh, Jee-Hwan, and Jan-Peter van Pijkeren. "CRISPR—Cas9-assisted recombineering in Lactobacillus reuteri." *Nucleic acids research* 42.17 (2014): e131-e131.

Oh, Phaik Lyn, et al. "Diversification of the gut symbiont Lactobacillus reuteri as a result of host-driven evolution." *The ISME journal* 4.3 (2010): 377-387.

Paez-Espino, David, et al. "Strong bias in the bacterial CRISPR elements that confer immunity to phage." *Nature communications* 4 (2013): 1430.

Palffy, R., et al. "Bacteria in gene therapy: bactofection versus alternative gene therapy." *Gene Therapy* 13.2 (2006): 101-105.

(56) References Cited

OTHER PUBLICATIONS

Pfaffl, Michael W. "A new mathematical model for elative quantification in real-time RT-PCR." *Nucleic acids research* 29.9 (2001): e45-e45.

Pfaffl, Michael W., Graham W. Horgan, and Leo Dempfle. "Relative expression software tool (REST©) for group-wise comparison and statistical analysis of relative expression results in real-time PCR." *Nucleic acids research* 30.9 (2002): e36-e36.

Rajpal, Gautam, et al. "Single-chain insulins as receptor agonists." *Molecular endocrinology* 23.5 (2009): 679-688.

Riboulet-Bisson, Eliette, et al, "Effect of Lactobacillus salivarius bacteriocin Abp118 on the mouse and pig intestinal microbiota." *PloS one* 7.2 (2012): e31113.

Riedel, Christian U., et al. "Improved luciferase tagging system for Listeria monocytogenes allows real-time monitoring in vivo and in vitro." *Applied and environmental microbiology* 73.9 (2007): 3091-3094.

Robert, Sofie, and Lothar Steidler. "Recombinant Lactococcus lactis can make the difference in antigen-specific immune tolerance induction, the Type 1 Diabetes case." *Microbial cell factories* 13.1 (2014): S11.

Rosche, William A., and Patricia L. Foster. "Determining mutation rates in bacterial populations." *Methods* 20.1 (2000): 4-17.

Sabat, Robert, Wenjun Ouyang, and Kerstin Wolk. "Therapeutic opportunities of the IL-22-IL-22R1 system," *Nature reviews Drug discovery* 13.1 (2014): 21-38.

Schaefer, Laura, et al. "The antimicrobial compound reuterin (3-hydroxypropionaldehyde) induces oxidative stress via interaction with thiol groups." *Microbiology* 156.6 (2010): 1589-1599.

Sheehan, Michelle M., et al. "Identification and characterization of a lysis module present in a large proportion of bacteriophages infecting *Streptococcus thermophilus*" *Applied and environmental microbiology* 65.2 (1999): 569-577.

Shi, Yibo, et al. "Characterization and determination of holin protein of *Streptococcus suis* bacteriophage SMP in heterologous host." *Virology journal* 9.1 (2012): 70.

Singh, Kailash, et al. "Interleukin-35 administration counteracts established murine type 1 diabetes—possible involvement of regulatory T cells." *Scientific reports* 5 (2015).

Sovran, Bruno, et al. "IL-22-STAT3 pathway plays a key role in the maintenance of ileal homeostasis in mice lacking secreted mucus barrier." *Inflammatory bowel diseases* 21. (2015): 531-542.

Spinler, Jennifer K., et al. "Human-derived probiotic Lactobacillus reuteri demonstrate antimicrobial activities targeting diverse enteric bacterial pathogens." *Anaerobe* 14.3 (2008): 166-171.

Steidler, Lothar, et al. "Treatment of murine colitis by Lactococcus lactis secreting interleukin-10." *Science* 289.5483 (2000): 1352-1355.

Sulakvelidze, Alexander, Zemphira Alavidze, and J. Glenn Morris. "Bacteriophage therapy." *Antimicrobial agents and chemotherapy* 45.3 (2001): 649-659.

Summers WC. Bacteriophage therapy. *Annu Rev Microbiol.* (2001); 55:437-51.

Sun, Jia, et al. "Pancreatic β-cells limit autoimmune diabetes via an immunoregulatory antimicrobial peptide expressed under the influence of the gut microbiota." *Immunity* 43.2 (2015): 304-317.

Sznol, Mario, et al. "Use of preferentially replicating bacteria for the treatment of cancer." *Journal of Clinical Investigation* 105.8 (2000): 1027.

Talarico, T. L., et al. "Production and isolation of reuterin, a growth inhibitor produced by Lactobacillus reuteri." *Antimicrobial agents and chemotherapy* 32.12 (1988): 1854-1858.

Tannock, Gerald W., et al. "Resource partitioning in relation to cohabitation of *Lactobacillus* species in the mouse forestomach." *The ISME journal* 6.5 (2012): 927-938.

Thomas, Carissa M., et al. "Histamine derived from probiotic Lactobacillus reuteri suppresses TNF via modulation of PKA and ERK signaling." *PluS one* 7.2 (2012): e31951.

Van Pijkeren, Jan Peter, and Robert A. Britton, "Precision genome engineering in lactic acid bacteria." *Microbial cell factories* 13.1 (2014): S10.

Van Pijkeren, Jan Peter, et al. "A novel Listeria monocytogenes-based DNA delivery system for cancer gene therapy." *Human gene therapy* 21.4 (2010): 405-416.

Van Pijkeren, Jan-Peter, and Robert A. Britton. "High efficiency recombineering in lactic acid bacteria." *Nucleic acids research* 40.10 (2012): e76-e76.

Van Pijkeren, Jan-Peter, et al. "Exploring optimization parameters to increase ssDNA recombineering in Lactococcus lactis and Lactobacillus reuteri." *Bioengineered* 3.4 (2012): 209-217.

Wang, Ing-Nang, David L. Smith, and Ry Young. "Holins: the protein clocks of bacteriophage infections." *Annual Reviews in Microbiology* 54.1 (2000): 799-825.

Wang, Xiaoting, et al. "Interleukin-22 alleviates metabolic disorders and restores mucosal immunity in diabetes." *Nature* 514.7521 (2014): 237-241.

Wells, Jeremy M., et al. "Lactococcus lactis: high-level expression of tetanus toxin fragment C and protection against lethal challenge." *Molecular microbiology* 8.6 (1993): 1155-1162.

Zhang, Yingnan, et al. "Identification of a small peptide that inhibits PCSK9 protein binding to the low density lipoprotein receptor." *Journal of Biological Chemistry* 289.2 (2014): 942-955.

Zhou, You, et al. "PHAST: a fast phage search tool." *Nucleic acids research* 39.suppl_2 (2011): W347-W352.

\* cited by examiner

METHODS FOR SYSTEMICALLY DELIVERING POLYPEPTIDES AND MICROORGANISMS THEREFOR

STATEMENT REGARDING FEDERALLY SPONSORED RESEARCH

This invention was made with government support under CA101573 and CA102948 awarded by the National Institutes of Health. The government has certain rights in the invention.

FIELD OF THE INVENTION

The invention is directed to systemically delivering polypeptides to the bloodstream of a subject, such as through administering into the gastrointestinal tract of the subject a microorganism that produces and releases the polypeptides. The invention is also directed to microorganisms suitable for this purpose.

BACKGROUND

Polypeptides, such as enzymes, antibodies, hormones, cytokines, etc., are tremendously useful as therapeutic agents. However, routes for systemically introducing such polypeptides to a subject are limited. Oral administration of the polypeptides is typically not feasible, as the polypeptides are either degraded in the gastrointestinal tract or are blocked from reaching the bloodstream. Direct intravenous administration is therefore the major route by which polypeptides are systemically introduced.

Certain types of genetically engineered bacteria have been used as vehicles for locally delivering polypeptides to various tissues. Engineered *Lactococcus lactis*, for example, has been administered intragastrically for delivering polypeptides such as trefoil factors and interleukin-10 locally to intestinal/mucosal tissues. See Steidler et al. 2000 and Huyghebaert et al. 2005. However, a systemic increase in polypeptides delivered via *Lactococcus lactis* was not found.

Other types of genetically engineered bacteria have been used as vehicles for delivery of polypeptides to tumors in the body. An engineered *Bifidobacterium* strain, for example, has been shown to translocate from the gastrointestinal tract after oral administration and target to, replicate in, and express genes within tumors. See Cronin et al. 2010. This effect, however, depends on the unique ability of the *Bifidobacterium* to translocate from the gastrointestinal tract to extra-intestinal sites in the body. While *Bifidobacterium* may serve as a useful delivery vehicle for some purposes, the systemic distribution of the *Bifidobacterium* is potentially deleterious in certain subject populations such as immunocompromised patients.

Engineered bacteria capable of being administering into the gastrointestinal tract and delivering polypeptides in the bloodstream without systemic levels of the bacteria themselves being increased are needed.

SUMMARY OF THE INVENTION

The invention is directed to methods and microorganisms for systemically introducing a polypeptide in a bloodstream of a subject.

One method comprises administering into the gastrointestinal tract of the subject a bacterium configured to produce and release the polypeptide. The bacterium may comprise a recombinant gene configured to express the polypeptide. The bacterium is administered in an amount effective to introduce the polypeptide in the bloodstream of the subject, preferably in a detectable amount.

In some versions, the bacterium is administered in an amount effective to introduce the polypeptide in the bloodstream of the subject without the bacterium being substantially introduced in the bloodstream of the subject.

In some versions, the bacterium is administered in an amount effective to introduce the polypeptide in the bloodstream in an amount effective to induce at least one direct systemic effect in the subject. In some versions, the bacterium is administered in an amount effective to introduce the polypeptide in the bloodstream in an amount effective to induce at least one direct effect in a non-gastrointestinal tissue in the subject. In some versions, the bacterium is administered in an amount effective to introduce the polypeptide in the bloodstream in an amount effective to induce at least one direct effect in a tissue selected from the group consisting of liver, muscles, lungs, kidneys, pancreas, and adipose tissue in the subject.

In some versions, the subject suffers from a condition treatable with systemic introduction of the polypeptide. In some versions, the subject suffers from a condition treatable with systemic introduction of the polypeptide but not treatable with local introduction of the polypeptide to the gastrointestinal tract without systemic introduction of the polypeptide. In either case, the polypeptide is introduced in the bloodstream of the subject in an amount effective to treat the condition, independent of the bacterium getting into the bloodstream.

In some versions, the polypeptide is a therapeutic polypeptide.

In some versions, the polypeptide is selected from the group consisting of a cytokine, a hormone, an antibody, an antimicrobial peptide, and an antigenic peptide.

In some versions, the polypeptide is selected form the group consisting of IL-22, IL-35, insulin, leptin, cathelicidin related antimicrobial peptide, a peptide inhibitor of PCSK9, and an endolysin.

In some versions, the subject suffers from at least one condition selected from the group consisting of insulin resistance, hyperglycemia, lipid dysregulation, hyperlipidemia, and obesity, and wherein the polypeptide is introduced in the bloodstream of the subject in an amount effective to treat the at least one condition.

In some versions, the bacterium comprises a bacterium other than a member of the *Bifidobacterium* genus. In some versions, the bacterium comprises a member of lactic acid bacteria, such as a member of lactic acid bacteria other than a member of the *Lactococcus* genus. In some versions, the bacterium comprises a member of *Lactobacillus*, such as *Lactobacillus reuteri*.

A microorganism of the invention comprises a bacterium comprising a recombinant gene configured to express a polypeptide, wherein the bacterium is configured to produce and release the polypeptide and is capable of introducing the polypeptide in the bloodstream of the subject.

In some versions, the bacterium is capable of introducing the polypeptide in the bloodstream of the subject without the bacterium being substantially introduced in the bloodstream of the subject.

In some versions, the polypeptide is capable of treating a condition in a subject with systemic introduction of the polypeptide in the subject.

In some versions, the polypeptide is selected form the group consisting of IL-22, IL-35, insulin, leptin, cathelicidin related antimicrobial peptide, a peptide inhibitor of PCSK9, and an endolysin.

In some versions, the bacterium comprises a bacterium other than a member of the *Bifidobacterium* genus. In some versions, the bacterium comprises a member of lactic acid bacteria, such as a member of lactic acid bacteria other than a member of the *Lactococcus* genus. In some versions, the bacterium comprises a member of *Lactobacillus*, such as *Lactobacillus reuteri*.

The objects and advantages of the invention will appear more fully from the following detailed description of the preferred embodiment of the invention made in conjunction with the accompanying drawings.

BRIEF DESCRIPTION OF THE DRAWINGS

FIG. 3A shows mIL-22 secretion from *L. reuteri* cells harboring the pVPL3461 plasmid compared to wild-type *L. reuteri* cells as a control. FIG. 3B shows mIL-22 secretion from *L. reuteri* cells harboring a chromosomal copy of a mIL-22 gene compared to wild-type *L. reuteri* cells as a control.

FIG. 9A shows length measurements at T0. FIG. 9B shows growth at T7. FIG. 9C shows length measurements of live versus dead animals.

FIG. 11A shows differences in BMI over the course of seven weeks of treatment (T7-T0). FIG. 11B shows differences in BMI over the course of six weeks of treatment (T7-T1, wherein T1 refers to the time after one week of treatment).

DETAILED DESCRIPTION OF THE INVENTION

Figure 1A:
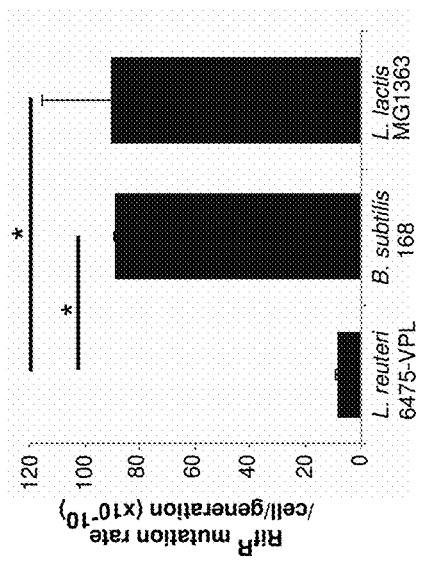
FIGS. 1A and 1B show mutation rates of various types of bacteria.

The invention provides microorganisms such as bacteria that are capable of introducing polypeptides in the bloodstream of a subject. The invention provides microorganisms such as bacteria that are more specifically capable of introducing the polypeptide in the bloodstream of the subject without the microorganism itself being substantially introduced in the bloodstream of the subject. The invention also provides microorganisms such as bacteria that are capable of introducing the polypeptide systemically in the subject without the microorganism itself being substantially introduced systemically in the subject. "Introduce" and its grammatical equivalents refer to delivery to a site in the body. The introducing may result in detectable presence at that site. "Systemically introduce" and its grammatical equivalents refer to delivery to the bloodstream or sites in the body via the bloodstream. The systemic introducing may result in detectable presence in the bloodstream or such sites. The sites in which the polypeptides are systemically introduced include sites or tissues perfused with the bloodstream and which are permeable to polypeptides. The sites in which the polypeptides are systemically introduced include sites or tissues other than those in the gastrointestinal tract. Exemplary sites or tissues include the liver, muscles, lungs, kidneys, pancreas, adipose tissue, or any other site or tissue in the body.

The bacteria of the invention include certain commensal or probiotic bacteria. The bacteria may include non-pathogenic, Gram-positive bacteria capable of anaerobic growth. The bacteria are preferably viable in the gastrointestinal tract of mammals. The bacteria may be food grade.

Exemplary bacteria include species of lactic acid bacteria (i.e., species of the order Lactobacillales). The bacteria may include species of lactic acid bacteria other than species of the *Lactococcus* genus. The bacteria may include species other than species of the *Bifidobacterium* genus Exemplary bacteria more preferably include species of the *Lactobacillus* genus.

Exemplary species from the *Lactobacillus* genus include *L. acetototerans*, *L. acidifarinae*, *L. acidipiscis*, *L. acidophi-*

*lus, L. agilis, L. algidus, L. atimentarius, L. amytolyticus, L. amylophilus, L. amylotrophicus, L. amylovorus, L. animatis, L. antri, L. apodemi, L. aviarius, L. bifermentans, L. brevis, L. buchneri, L. camelliae, L. casei, L. catenaformis, L. ceti, L. coleohominis, L. collinoides, L. composti, L. concavus, L. coryniformis, L. crispatus, L. crustorum, L. curvatus, L. delbrueckii* subsp. *delbrueckii, L. delbrueckii* subsp. *butgaricus, L. delbrueckii* subsp. *lactis, L. dextrinicus, L. diolivorans, L. equi, L. equigenerosi, L. farraginis, L. farciminis, L. fermentum, L. fornicalis, L. fructivorans, L. frumenti, L. fuchuensis, L. gallinarum, L. gasseri, L. gastricus, L. ghanensis, L. graminis, L. hammesii, L. hamsteri, L. harbinensis, L. hayakitensis, L. helveticus, L. hitgardii, L. homohiochii, L. iners, L. ingluviei, L. intestinalis, L. jensenii, L. johnsonii, L. katixensis, L. kefiranofaciens, L. kefiri, L. kimchii, L. kitasatonis, L. kunkeei, L. leichmannii, L. lindneri, L. malefermentans, L. mati, L. manihotivorans, L. mindensis, L. mucosae, L. murinus, L. nagelii, L. namurensis, L. nantensis, L. oligofermentans, L. oris, L. panis, L. pantheris, L. parabrevis, L. parabuchneri, L. paracollinoides, L. parafarraginis, L. parakefiri, L. paratimentarius, L. paraplantarum, L. pentosus, L. perolens, L. plantarum, L. pontis, L. psittaci, L. rennini, L. reuteri, L. rhamnosus, L. rimae, L. rogosae, L. rossiae, L. ruminis, L. saerimneri, L. sakei, L. salivarius, L. sanfranciscensis, L. satsumensis, L. secaliphilus, L. sharpeae, L. siliginis, L. spicheri, L. suebicus, L. thailandensis, L. ultunensis, L. vaccinostercus, L. vaginalis, L. versmoldensis, L. vini, L. vitulinus, L. zeae,* and *L. zymae.*

A particularly preferred bacterium is *L. reuteri*.

A bacterium that can bind mucus in the gastrointestinal tract is preferred but not required. We surmise that binding mucus in the gastrointestinal tract may place the bacterium in close proximity to epithelial cells. Release of polypeptides so close to the epithelial cells may help systemic delivery of the polypeptides. A bacterium capable of binding mucus is *L. reuteri*, such as *L. reuteri* VPL1014, discussed below in the examples. The ability to bind mucus can be mediated by the presence of a mucus-binding protein, such as the cell-mucus binding protein CmbA (Jensen et al. 2014).

The bacterium preferably has a low mutation rate. The bacterium preferably has a mutation rate of less than about $100\times10^{-10}$ mutations per cell per generation, less than about $60\times10^{-10}$ mutations per cell per generation, and more preferably less than about $20\times10^{-10}$ mutations per cell per generation.

The bacterium may be engineered to express a polypeptide of interest. The bacterium accordingly may comprise a recombinant gene configured to express the polypeptide of interest. The bacterium may alternatively or additionally comprise a recombinant DNA sequence that results in increased expression of the polypeptide of interest. "Recombinant" used in reference to a gene refers herein to a sequence of nucleic acids that are not naturally occurring in the genome of the bacterium. The non-naturally occurring sequence may include a recombination, substitution, deletion, or addition of one or more bases with respect to the nucleic acid sequence originally present in the natural genome of the bacterium. "Gene" refers to the collection of genetic elements involved in expressing a coding sequence and may include, in addition to the coding sequence, a promoter, a ribosomal binding site, an enhancer, etc. In some versions, increased expression of the polypeptide of interest can result from introducing or modifying (e.g., recombining, substituting, deleting, etc.) genes or other genetic elements responsible for regulating expression of the polypeptide of interest, such as genes for transcription factors or signaling factors.

The bacterium may be engineered to produce and release the polypeptide. As used herein, "release" used with respect to the bacterium releasing the polypeptide refers to disposing the polypeptide outside the bacterium, i.e., in the extracellular environment of the microorganism. Release may occur through secretion of the polypeptide or through lysis of the bacterium, among other possible mechanisms. Elements for engineering a bacterium to secrete a polypeptide are well known in the art. Typical elements include a signal peptide-encoding sequence placed upstream of—and in-frame with—the coding sequence of the polypeptide to be secreted. The sequences of a large number of signal peptides for bacteria are known in the art. Exemplary signal peptide sequences are available at www.cbs.dtu.dk/services/SignalP/. Elements for inducing a bacterium to lyse include lytic proteins, which can be expressed from a bacterium through recombinant engineering. As used herein, "lytic protein" refers to any protein that causes or aids in the lysis of a microorganism.

Lytic proteins are well known in the art. A number of lytic proteins, for example, are found in bacteriophages and serve to lyse microorganisms during the lytic stages of the bacteriophage's life cycle. These include holins and lysins (Sheehan et al. 1999). During bacteriophage replication, biologically active lysins are present in the cytosol but require expression of a membrane protein, holin, to release the virions from the cell. When holin levels are optimal, the lysin can access the peptidoglycan layer for cleavage which leads to bacterial cell lysis (Wang et al. 2000). So far, five main groups of lysins have been identified that can be distinguished from one and another based on the cleavage specificity of the different bonds within the peptidoglycan (Fischetti 2009). Structurally, lysins can consist of a single catalytic domain, which generally is typical for lysins derived from bacteriophages targeting Gram-negative bacteria (Cheng et al. 1994). Bacteriophages targeting Gram-positive bacteria typically encode lysins that contain multiple domains: a N-terminal catalytic domain and a C-terminal cell-wall binding domain (Nelson et al. 2006, Navarre et al. 1999). A few lysins have been identified that have three domains (Becker et al. 2009).

A number of other lytic proteins are native to the microorganisms themselves (Feliza et al. 2012, Jacobs et al. 1994, Jacobs et al. 1995, López et al. 1997). These lytic proteins may affect cell wall metabolism or introduce nicks in the cell wall. Five protein classes are differentiated by the wall component they attack (Loessner et al. 2005, Loessner et al. 2002).

In some versions of the invention, the microorganism is configured to constitutively express a lysin and to express a holin in a maltose-dependent manner. In some versions, the microorganism is configured to express both a lysin and a holin in a maltose-dependent manner.

Lytic proteins can be expressed in a maltose-dependent manner by operably connecting the coding sequence of the lytic protein to a maltose-sensitive promoter. "Coding sequence" refers to a nucleic acid in a gene that encodes the gene product. "Promoter" refers to any nucleic acid that confers, activates, or enhances expression of an operably connected coding sequence. "Operably connected" generally refers to a connection of two genetic elements in a manner wherein one can operate on or have effects on the other. "Operably connected" used in reference to a promoter and a coding sequence refers to a connection between the promoter and the coding sequence such that the coding sequence is under transcriptional control of the promoter. For example, promoters are generally positioned 5' (upstream) of a coding sequence to be operably connected to the promoter. In the construction of heterologous promoter/coding sequence combinations, it is generally preferred to position the promoter at a distance from the transcription start site that is approximately the same as the distance between that promoter and the coding sequence it controls in its natural setting, i.e. in the gene from which the promoter is derived. As is known in the art, some variation in this distance can be accommodated without loss of promoter function.

Operably connecting a maltose-inducible promoter to the coding sequence of a lytic protein induces lysis of the microorganism, release of the lytic protein, and release of any other polypeptides made by the microorganism, in a maltose-dependent manner. Such release occurs in the gastrointestinal tract due to natural levels of maltose therein.

An exemplary maltose-inducible promoter is represented by SEQ ID NO: 1, which is a maltose-inducible promoter found in *L. reuteri*. The maltose-inducible promoter represented by SEQ ID NO: 1 or variants thereof are suitable for use in the present invention. Variants of SEQ ID NO:1 include sequences at least about 80% identical, at least about 83% identical, at least about 85% identical, at least about 87% identical, at least about 90% identical, at least about 83% identical, at least about 95% identical, at least about 97% identical, at least about 98% identical, or at least about 99% identical to SEQ ID NO: 1 Other methods of inducing lysis of bacteria in vivo are known.

The bacteria can be engineered using any methods known in the art. General methods are provided in Green et al. 2012. Methods for engineering lactic acid bacteria such as *L. lactis* are provided by van Pijkeren et al. 2012, Oh et al. 2014, and Barrangou et al. 2016.

The recombinant gene may be incorporated into the chromosome of the bacterium or may be included on an extra-chromosomal plasmid. The extra-chromosomal plasmid may replicate at any copy number in the cell and, accordingly, be a single-copy plasmid, a low-copy plasmid, or a high-copy plasmid. The extra-chromosomal plasmid is preferably substantially stable within the bacterium. The rate of loss of the extra-chromosomal plasmid from the bacterium is preferably less than about 10% per generation, less than about 5% per generation, or less than about 1% per generation, wherein percent per generation refers to the percent of the population per generation in which the plasmid is lost.

The bacterium may be engineered to produce and release any polypeptide of interest. The polypeptide may have any of a number of amino acid chain lengths. In some versions, the polypeptide may have an amino acid chain length of from about 2 to about 4000 amino acids, from about 2 to about 3000 amino acids, from about 2 to about 2000 amino acids, from about 2 to about 1500 amino acids, from about 2 to about 1000 amino acids, from about 2 to about 500 amino acids, from about 3 to about 250 amino acids, or from about 3 to about 225 amino acids. The polypeptide may have a net positive charge at neutral pH, a net negative charge at neutral pH, or a net neutral charge at neutral pH. The polypeptide is preferably soluble in water. The polypeptide may form a globular or fibrous structure or may have an intrinsically disordered structure.

The polypeptide may have any of a number of functionalities. The polypeptide, for example, may be enzymatic or non-enzymatic. The polypeptide may be fluorescent or non-fluorescent. Within the physiological context of a mammal, the polypeptide may be a cytokine, a hormone, an antibody, an antimicrobial peptide, and an antigenic peptide, among others.

Exemplary classes of cytokines include interleukins, lymphokines, monokines, interferons (IFNs), colony stimulating factors (CSFs), among others. Specific exemplary cytokines include IL-1 alpha (IL1a), IL-1 beta (IL1b), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, IL-36, IFN-alpha, IFN-beta IFN-gamma, TNF-alpha, TNF-beta, CNTF (C-NTF), LIF, OSM (oncostatin-M), EPO (erythropoietin), G-CSF (GCSF), GM-CSF (GMCSF), M-CSF (MCSF), SCF, GH (growth hormone), PRL (prolactin), aFGF (FGF-acidic), bFGF (FGF-basic), INT-2, KGF (FGF7). EGF, TGF-alpha, TGF-beta, PDGF, betacellulin (BTC), SCDGF, amphiregulin, and HB-EG, among others.

Exemplary hormones include epinephrine, melatonin, triiodothyronine, thyroxine, amylin (or islet amyloid polypeptide), adiponectin, adrenocorticotropic hormone (or corticotropin), angiotensinogen, angiotensin, antidiuretic hormone (or vasopressin, arginine vasopressin), atrial-natriuretic peptide (or atriopeptin), brain natriuretic peptide, calcitonin, cholecystokinin, corticotropin-releasing hormone, cortistatin, encephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, insulin-like growth factor (or somatomedin), leptin, lipotropin, luteinizing hormone, melanocyte stimulating hormone, motilin, orexin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone (or thyrotropin), thyrotropin-releasing hormone, and vasoactive intestinal peptide, among others.

Other physiologically active peptides include glucagon-like peptide-1 (GLP-1); tachykinin peptides, such as substance P, kassinin, neurokinin A, eledoisin, and neurokinin B; peptide PHI 27 (peptide histidine isoleucine 27); pancreatic polypeptide-related peptides, such as NPY (neuropeptide Y), PYY (peptide YY), and APP (avian pancreatic polypeptide); opioid peptides, such as proopiomelanocortin (POMC) peptides and prodynorphin peptides; AGG01; B-type natriuretic peptide (BNP); lactotripeptides; and peptides that inhibit PCSK9 (Zhang et al. 2014).

Exemplary antibodies include single-chain antibodies, single-domain antibodies (sdAbs), and single-chain variable fragments (scFvs).

Exemplary antimicrobial peptides include cathelicidins, defensins, protegrins, mastoparan, poneratoxin, cecropin, moricin, melittin, magainin, dermaseptin, and others.

In preferred versions, the polypeptide that is systemically introduced is a polypeptide capable of treating a condition in a subject with its systemic introduction. In some versions, The polypeptide that is systemically introduced is a polypeptide capable of treating a condition in a subject with its systemic introduction but is not capable of treating a condition in the subject with its local introduction to the gastrointestinal tract alone. The condition may be any condition described herein.

The inventors have unexpectedly found that administering *L. reuteri* to the gastrointestinal tract is capable of delivering produced polypeptides to the bloodstream without the bacteria themselves being introduced in the bloodstream. Accordingly, an aspect of the invention includes administering an amount of a bacterium of the invention into the gastrointestinal tract of a subject. The bacterium may be administered in any amount effective to introduce the polypeptide in the bloodstream of the subject. Exemplary amounts include from about $1\times10^3$ to about $1\times10^{15}$, from about $1\times10^5$ to about $1\times10^{13}$, from about $1\times10^7$ to about $1\times10^{11}$, or about $1\times10^9$ colony forming units (CFU). Amounts above and below these ranges may be acceptable.

The bacterium can be administered to the gastrointestinal tract by any method known in the art. The bacterium may be administered orally, rectally, or directly into the gastrointestinal tract via a stoma. The bacterium is preferably administered directly into or upstream of the small intestines, so that the bacterium ultimately passes through or into the small intestines. The bacterium may be swallowed or introduced via a tube.

The bacterium may be combined in a composition with a pharmaceutically acceptable excipient, carrier, buffer, stabilizer or other material well known to those skilled in the art. Such materials should be non-toxic and should not interfere with the efficacy of the bacterium. The precise nature of the carrier or other material may depend on the route of administration. The composition may be liquid, solid, or semi-solid. The composition may comprise a foodstuff or may take the form of a pharmaceutical composition. Those of relevant skill in the art are well able to prepare suitable compositions.

The subject to which the bacterium is administered may be an animal, such as a mammal or, more specifically, a human.

In some versions of the invention, the bacterium is administered in an amount effective to introduce the polypeptide in the bloodstream in an amount effective to induce at least one systemic effect in the subject, such as at least one effect in a non-gastrointestinal tissue in the subject. As used herein, "systemic effect" refers to an effect that occurs at a site or tissue in the body other than where the polypeptide is initially released from the bacterium. In the present case, the term refers to an effect that occurs at a site or tissue other than the gastro-intestinal tract, such as the liver, muscles, lungs, kidneys, pancreas, adipose tissue, or others. The systemic effect preferably occurs by virtue of the polypeptide being systemically introduced and accessing a site or tissue other than gastrointestinal tissue via bloodstream, such that the effect is a direct effect of the polypeptide and is not a secondary effect of a primary effect of the polypeptide in the gastrointestinal tissue. Such effects are referred to herein as "direct systemic effects." Direct systemic effects of the systemically introduced polypeptide can be distinguished from secondary effects, for example, by comparing effects resulting from administering the polypeptide-producing bacterium into the gastrointestinal tract with effects resulting from systemically administering the polypeptide directly into the bloodstream and effects resulting from locally administering the polypeptide directly into the gastrointestinal tract. Direct systemic effects are those that are mirrored by the systemic administration of the polypeptide into the bloodstream but not the local administration of the polypeptide into the gastrointestinal tract. The presence of direct systemic effects of the polypeptide resulting from administering the polypeptide-producing bacterium into the gastrointestinal tract can be an indicator of the polypeptide entering the bloodstream, whether or not the polypeptide itself is detected in the bloodstream.

In some versions, the bacterium is administered to a subject that suffers from a condition treatable with systemic introduction of the polypeptide. In yet other versions, the bacterium is administered to a subject that suffers from a condition treatable with systemic introduction of the polypeptide but is not treatable with only local introduction of the polypeptide to the gastrointestinal tract. In either case, the polypeptide is introduced in the bloodstream of the subject in an amount effective to treat the condition. As used herein, "treat" used in reference to a condition refers to ameliorating to any extent the condition itself or any symptom associated therewith.

In some versions, the bacterium is administered to a subject to prevent or inhibit the development of any of the conditions or associated symptoms described herein. The subject in such a case may show early signs of the condition or symptom, have a genotype that predisposes the subject to develop the condition or symptom, have a behavior or environmental situation that predisposes the subject to develop the condition or symptom, or otherwise be predisposed to develop the condition or symptom.

A particular aspect of the invention is directed to introducing interleukin-22 (IL-22) in the bloodstream of a subject by administering a bacterium comprising a recombinant interleukin-22 (IL-22) gene. The IL-22 may be introduced in the bloodstream of the subject in an amount effective to induce at least one IL-22-dependent effect in a non-gastrointestinal tissue in the subject. An exemplary IL-22 that can be systemically introduced comprises a sequence of SEQ ID NO:2 or a sequence at least about 90%, 95%, 97%, 99% or more identical thereto.

IL-22 is capable of inducing a number of effects in non-gastrointestinal tissues when circulating systemically through the bloodstream. In respiratory epithelial cells, for example, IL-22 can increase antibacterial defense, elevate mucus production, enhance proliferation, and raise production of granulocyte-attracting chemokines. In synovial fibroblasts, IL-22 can elevate RANKL expression and increase production of monocyte-attracting chemokines. In pancreatic cells, IL-22 can increase protection against damage, inhibit autophagy, and enhance islet proliferation. In hepatocytes, IL-22 can increase acute-phase protein production, increase protection against damage, and elevate liver progenitor cell proliferation. In epidermal keratinocytes, IL-22 can increase antibacterial defense, retard differentiation and cornification, induce production of granulocyte-attracting chemokines, elevate migration and tissue remodeling, and enhance STAT3 and IL-20 expression. See Sabat et al. 2014 and Wang et al. 2014 for additional direct IL-22-dependent effects.

Another particular aspect of the invention is directed to introducing interleukin-22 (IL-22) in the bloodstream of a diabetic subject by administering a bacterium comprising a recombinant interleukin-22 (IL-22) gene. The diabetic subject may suffer from type 1 or type 2 diabetes. IL-22 has been shown to have a number of ameliorative effects in diabetic subjects. In type 2 diabetic subjects, these effects include ameliorating hyperglycemia, insulin resistance, hyperlipidemia, lipid dysregulation in the liver and adipose tissues, endotoxemia, and chronic inflammation. See Wang et al. 2014. As shown in the present examples, IL-22 is also capable of reducing body mass index (BMI).

More generally, subjects in which IL-22 is introduced may include those suffering from of insulin resistance, hyperglycemia, lipid dysregulation, hyperlipidemia, obesity, or other manifestations of metabolic syndrome. The systemic effect of the systemic introduction of IL-22 to such subjects may include a reduction in body mass index (BMI), liver weight, liver triglycerides, glucose intolerance, and insulin resistance, or other effects described elsewhere herein.

Another polypeptide that may be introduced in the bloodstream of a subject with the bacteria of the invention is interleukin-35 (IL-35). Systemic administration of IL-35 treats type-1 diabetes and inhibits or slows the development of type-1 diabetes. See Singh et al. 2015. An exemplary IL-35 that can be systemically introduced is a human recombinant IL-35 comprising a sequence of SEQ ID NO:3 or a sequence at least about 90%, 95%, 97%, 99% or more identical thereto. Bacteria of the invention comprising a recombinant IL-35 gene can be administered to subjects with diabetes, such as type 1 diabetes, to systemically introduce the IL-35 polypeptide in the bloodstream of the subject in an amount effective to treat the diabetes in the subject.

Another polypeptide that may be introduced in the bloodstream of a subject with the bacteria of the invention is insulin. The insulin can be produced in single-chain form. See, e.g., Rajpal et al. 2009. An exemplary insulin that can be systemically introduced includes the insulin A-chain connected to the insulin B-chain by the linker sequence QRGGGGGQR (SEQ ID NO:4). See Rajpal et al. 2009. Single-chain insulin retains all of the physiological effects of traditional two-chain insulin, including stimulation of glucose uptake into adipocytes, and suppression of hepatic gluconeogenesis. Bacteria of the invention comprising a recombinant insulin gene can be administered to subjects with diabetes, insulin resistance, or hyperglycemia to systemically introduce the insulin polypeptide in the bloodstream of the subject in an amount effective to treat the diabetes, or hyperglycemia in the subject.

Another polypeptide that may be introduced in the bloodstream of a subject with the bacteria of the invention is leptin. Leptin is made by adipose tissue and regulates energy balance by acting on receptors in the brain. Congenital leptin deficiency (CLD), or generalized lipodystrophy results in a lack of leptin and can lead to a litany of disorders, including morbid obesity (in the case of CLD), diabetes, and infertility. Systemic leptin replacement therapy mitigates these disorders. An exemplary leptin polypeptide that can be systemically introduced includes a polypeptide comprising a sequence of SEQ ID NO:5 or a sequence at least about 90%, 95%, 97%, 99% or more identical thereto. Bacteria of the invention comprising a recombinant leptin gene can be administered to subjects with congenital leptin deficiency or generalized lipodystrophy to systemically introduce the leptin polypeptide in the bloodstream of the subject in an amount effective to treat the obesity, diabetes, infertility or any other aspect of the congenital leptin deficiency or generalized lipodystrophy.

Another polypeptide that may be introduced in the bloodstream of a subject with the bacteria of the invention is cathelicidin related antimicrobial peptide (CRAMP). CRAMP is a small peptide produced by pancreatic islets in response to gut microbiota-derived short-chain fatty acids. Synonyms for CRAMP include CAMP, CAP18, Cnlp, FALL39, and MCL. The islet-derived CRAMP maintains immune homeostasis. CRAMP production is defective in non-obese diabetic mice, leading to inflammation and activation of diabetogenic T-cells and resulting in type 1 diabetes (Sun et al. 2015). This process can be reversed by direct systemic administration of CRAMP. An exemplary CRAMP polypeptide that can be systemically introduced includes a polypeptide comprising a sequence of SEQ ID NO:6 or a sequence at least about 90%, 95%, 97%, 99% or more identical thereto. Bacteria of the invention comprising a recombinant CRAMP gene can be administered to non-obese diabetic subjects to systemically introduce the CRAMP polypeptide in the bloodstream of the subject in an amount effective to treat the diabetes and/or inflammation in these subjects.

Other polypeptides that may be introduced in the bloodstream of a subject with the bacteria of the invention include peptide inhibitors of PCSK9. PCSK9 (proprotein convertase subtilisin/kexin type 9) is a negative regulator of the hepatic low density lipoprotein receptor. Inhibition of PCSK9 results in LDL cholesterol-lowering effects. A number of peptide inhibitors of PCSK9 are known in the art. See Zhang et al. 2014. Any of these polypeptides or others can be introduced in the bloodstream of a subject with the bacteria of the invention. A particularly preferred peptide inhibitor of PCSK9 is referred to as "Pep2-8," which comprises a sequence of SEQ ID NO:7. Bacteria of the invention comprising a recombinant gene configured to express one or more peptide inhibitors of PCKS9 can be administered to subjects with hypercholesterolemia to systemically introduce the peptide inhibitor of PCSK9 in the bloodstream of the subject in an amount effective to treat the hypercholesterolemia.

Other polypeptides that may be introduced in the bloodstream of a subject with the bacteria of the invention include lysins, such as bacteriophage-derived lysins (endolysins), i.e. enzybiotics. One of the largest concerns in 21st century medicine is the development of microbial antibiotic-resistance. Little progress has been made in the discovery and development of novel antibiotics, and bacteriophage-derived lysins (enzybiotics) constitute promising alternatives to antibiotics. The enzybiotics interfere with peptidoglycan cell wall synthesis, mainly of Gram positive bacteria, but do so in a species specific manner. Exemplary lysins that can be systemically introduced include those described in the references cited herein, all of which are incorporated herein by reference. Bacteria of the invention comprising a recombinant gene configured to express one or more lysins can be administered to subjects with sepsis or infection with pathogens such as *S. aureus* to systemically introduce the lysin in the bloodstream of the subject in an amount effective to treat the sepsis or infection.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Bacterial strains, plasmids, media, and culture.

Bacterial strains and plasmids used in the present examples are listed in Table 1. *Lactobacillus reuteri* VPL1014 and its derivatives were routinely cultured at 37° C. in deMan Rogosa Sharpe (MRS) medium (Difco, BD Biosciences). Where appropriate, erythromycin was added to a final concentration of 5 µg/ml. Competent cells of *L. reuteri* were prepared as described before (Ahrnd et al. 1992). To test IL-22 expression and to prepare bacteria for animal experiments, bacteria were cultured in Lactobacilli Defined Medium-III (LDM-III, Table 2).

Specifically, *L. reuteri* VPL1014 was inoculated in 10 ml MRS broth, and *L. reuteri* VPL3461 was inoculated in 10 ml MRS containing 5 g/ml erythromycin at 37° C. Overnight-cultures of each strain were sub-cultured in MRS at $OD_{600}$=0.1. At OD600≥1≤1.2 cells were harvested by centrifugation (5,000 rpm for 5 min), and the cell pellets were washed twice with LDM-III. Washed cell pellets, each derived from 10-ml culture, were stored at −80° C. until use. From this step onwards, no antibiotics were supplemented to the culture media. At the day of gavaging, the cell pellets were resuspended in 10 ml freshly prepared pre-warmed LDM-III and incubated at 37° C. until $OD_{600}$≥3.5≤3.7. Bacteria were concentrated 10-fold, and suspensions were made containing ~$10^{10}$ CFU/ml *L. reuteri* VPL1014 or VPL3461. For animal experiments (see below) 100 al of the suspension was administrated by oral gavage to the corresponding animals.

TABLE 1

Bacterial strains and plasmids used in the present examples.

| Strain or plasmid | Characteristics | Source |
|---|---|---|
| *L. reuteri* VPL1014 | A derivative of *L. reuteri* ATCC PTA 6475, human breast milk isolate | ATCC PTA 6475, U.S. Pat. 7,344,867 to BioGaia AB (Lerum, SE), and van Pijkeren et al. 2012 |
| *L. reuteri* VPL3461 | *L. reuteri* VPL1014 harboring pVPL3461 | Described herein |
| pJP028 | $Em^R$, derivative of pNZ8048 containing promoter from *L. reuteri* SD2112, signal peptide from *L. reuteri* JCM1112, and LPXTG (cell wall anchor domain) | Described herein |
| pVPL3461 | $Em^R$, derivative of pJP028 omitting LPXTG domain and harboring mIL-22 gene | Described herein |

TABLE 2

Lactobacilli Defined Medium-III (LDM3) composition.

| Basal Medium | | |
|---|---|---|
| Ingredient | Amount per Liter | |
| $K_2HPO_4$. | 1.50 g | |
| $KH_2PO_4$ | 1.50 g | |
| Sodium Acetate | 15.00 g | |
| Sodium Citrate, Dihydrate | 0.25 g | |
| Tryptophan | 0.05 g | |
| Asparagine, Monohydrate | 0.23 g | |
| Vitamin-free Casamino acid | 10.00 g | |
| Cysteine-HCl, Monohydrate | 0.22 g | |
| Tween80 (10% v/v) | 10 ml | |

Dissolve in 937.5 ml of DI water and autoclave at 121° C. for 15 min. Prepare stock solutions (as below) and add to sterile Basal Medium.

| Vitamin Solution (in 25 ml $dH_2O$) | | |
|---|---|---|
| Thiamin HCl | 10 mg | 0.5 ml |
| p-aminobenzonoic acid | 2 mg | |
| Calcium pantothenic acid | 20 mg | |
| Niacin | 50 mg | |
| Pyridoxin HCl | 25 mg | |
| Biotin Solution (in 50 ml 0.01M HCl) | | |
| Biotin | 4 mg | 0.5 ml |
| 96% EtOH | 40 µL | |
| Riboflavin Solution (in 50 ml $dH_2O$) | | |
| Riboflavin | 4 mg | 5 ml |
| Folic Acid Solution (in 50 ml 0.001M NaOH) | | |
| Folic acid | 10 mg | 0.5 ml |
| Nucleic Acid Solution (in 15 ml 1M HCl) | | |
| Adenine hemisulfate | 50 mg | 3 ml |
| Guanine | 40.3 mg | |
| Cytidylic acid | 150 mg | |
| Uracil Solution (in 10 ml 1M NaOH) | | |
| Uracil | 200 mg | 1 ml |
| Thymidine Solution (in 12.5 ml $dH_2O$) | | |
| Thymidine | 20 mg | 1 ml |
| Salt Solution (in 10 ml $dH_2O$) | | |
| $MgSO_4$ | 0.793 g | 1 ml |

TABLE 2-continued

Lactobacilli Defined Medium-III (LDM3) composition.

| | |
|---|---|
| MnSO4 | 0.128 g |
| FeSO4 | 0.130 g |
| Glucose (40% w/v) | 50 ml |

Total 1 L (LDM), final pH6.5

Mutation Rate.

Figure 1B:
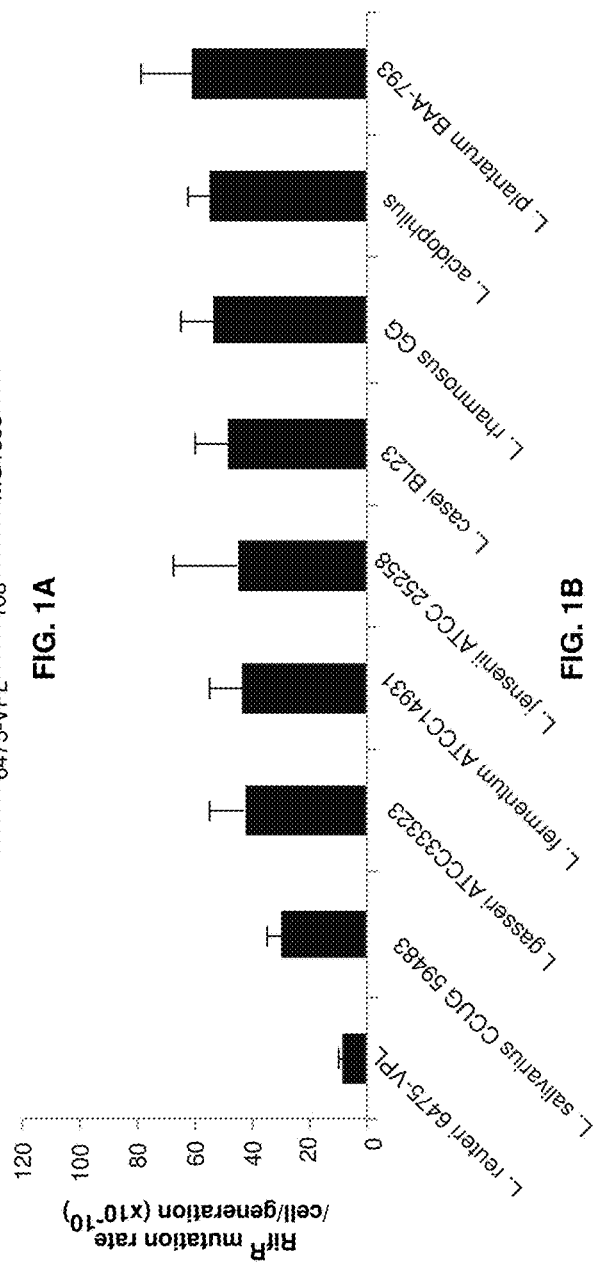

A suitable microorganism for delivering peptides preferably has a low mutation rate. The mutation rate of L. reuteri VPL1014 was compared with that of a number of other microorganisms using conventional methods (Rosche et al. 2000, Foster et al. 2006). As shown in FIGS. 1A and 1B, L. reuteri displayed an exceptionally low mutation rate, particularly compared to the other tested probiotic microorganisms.

Reagents and Enzymes.

Cloning was performed via ligation cycle reaction (LCR; Kok et al. 2014). Enzymes and reagents for LCR were purchased from Fermentas. Polymerase chain reaction (PCR) for cloning purposes was performed with the high-fidelity enzyme Phusion Hot Start Polymerase II (Fermentas). PCR for screening purposes was performed with Taq polymerase (Denville Scientific). To concentrate the LCR reaction prior to electrotransformation into L. reuteri, we used Pellet Paint Co-Precipitant (Novagen). Oligonucleotides and synthetic double-stranded DNA fragments were purchased from Integrated DNA Technologies. All oligonucleotides and synthetic DNA fragments used in this study are listed in Table 3.

TABLE 3

Oligonucleotides and synthetic DNA used in the present examples.

| Oligo-nucleo-tides | Sequence |
|---|---|
| oVPL329 | attccttggacttcatttactgggtttaac (SEQ ID NO: 8) |
| oVPL363 | taatatgagataatgccgactgtac (SEQ ID NO: 9) |
| oVPL1219 | ttcatggggatgaatgcttctgctaatacattaccagttaatactcgttg (SEQ ID NO: 10) |
| oVPL1220 | cttggttttctaattttggttcaaagatcaaacacaagcattacgtaaactc (SEQ ID NO: 11) |
| oVPL1221 | gcttgaaacgttcaattgaaatggca (SEQ ID NO: 12) |
| oVPL1222 | tgtaaaaccaataaggactgaagc (SEQ ID NO: 13) |
| oVPL1223 | ggagttgcttcagtccttattggttttacattcatggggatgaatgcttctgctaataca (SEQ ID NO: 14) |
| oVPL1224 | tgatctttgaaccaaaattagaaaaccaaggcttgaaacgttcaattgaaatggcaatta (SEQ ID NO: 15) |
| oVPL1313 | actccctgaagaatataccctcc (SEQ ID NO: 16) |
| oVPL1314 | cgctattgagcacagatacgag (SEQ ID NO: 17) |
| oVPL1315 | atgcttccccgtataaccatca (SEQ ID NO: 18) |
| oVPL1316 | ggccatatctgcatcataccag (SEQ ID NO: 19) |
| oVPL1321 | gatcaccgacaagggcctg (SEQ ID NO: 20) |
| oVPL1322 | ggctatgaaactcgtactgcc (SEQ ID NO: 21) |
| oVPL1325 | ggctgtattcccctccatcg (SEQ ID NO: 22) |
| oVPL1326 | ccagttggtaacaatgccatgt (SEQ ID NO: 23) |
| gVPL1 | ATTCATGGGGATGAATGCTTCTGCTAATACATTACCAGTTAATACTCGTTGTAAATTAGAAGTTAGTAATTTTCAACAACCATATATTGTTAATCGTACTTTTATGTTAGCTAAAGAAGCTAGTTTAGCTGATAATAATACTGATGTTCGTTTAATTGGTGAAAAATTATTTCGTGGTGTTAGTGCTAAAGATCAATGTTATTTAATGAAACAAGTTTTAAATTTTACTTTAGAAGATGTTTTATTACCACAAAGTGATCGTTTTCAACCATATATGCAAGAAGTTGTTCCATTTTTAACTAAATTAAGTAATCAATTAAGTAGTTGTCATATTAGTGGTGATGATCAAAATATTCAAAAAAATGTTCGTCGTTTAAAAGAAACTGTTAAAAAATTAGGTGAAAGTGGTGAAATTAAAGCTATTGGTGAATTAGATTTATTATTTATGAGTTTACGTAATGCTTGTGTTTGATCTTTGAACCAAAATTAGAAAACCAAGG (SEQ ID NO: 24) |

Construction of L. reuteri VPL1014 that Secretes mIL-22.

Figure 2:
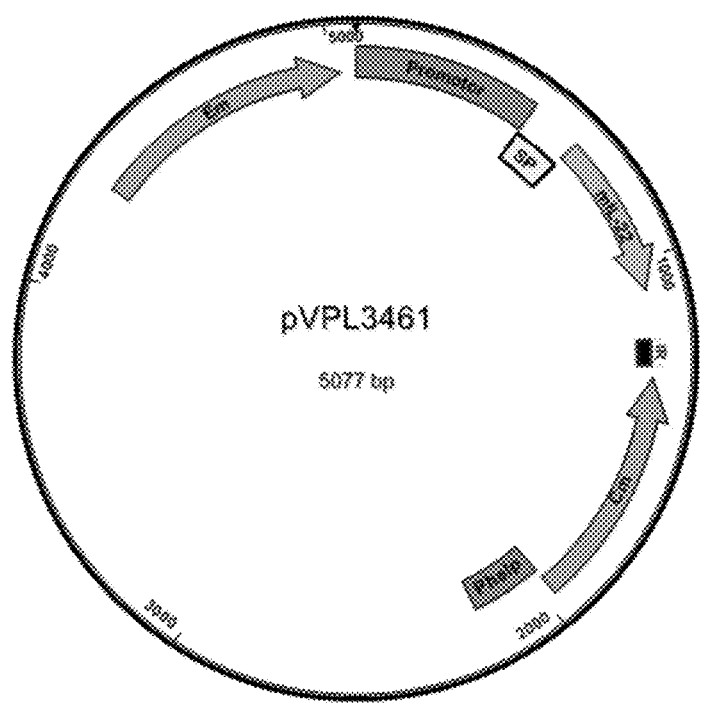
FIG. 2 is a plasmid map of the pVPL3461 murine interleukin-22 (mIL-22)-expressing plasmid of the invention, showing an erythromycin resistance gene (Em), an chloramphenicol resistance gene coding sequence (Cm), a phelp promoter (Phelp) (Riedel et al. 2007) for the chloramphenicol resistance gene coding sequence, an mIL-22 coding sequence (mIL-22), a signal peptide for secretion of mIL-22 (SP), a promoter for the signal peptide and the mIL-22 coding sequence (Promoter), and an inverted repeat (IR), which serves as a transcriptional terminator.

Our aim was to engineer Lactobacillus reuteri VPL1014 to secrete the murine cytokine interleukin-22 (mIL-22). We first opted for expression from the multicopy plasmid pJP028 to maximize mIL-22 production. pJP028 is a derivative of pNZ8048 (de Ruyter et al. 1996) in which the nisin-expression cassette was replaced with a secretion cassette. By PCR (oVPL1221-oVPL1222), we amplified the backbone of pJP028, omitting the cell wall anchor domain, to yield a 4.579 kb product. For optimal expression of mIL-22 in our expression host, L. reuteri, we first applied in-silico codon optimization of the mIL-22 coding sequence using the online software, OPTIMIZER (genomes.urv.es/OPTIMIZER/, Table 4) followed by synthesis. The resulting synthetic product (gVPL1) was amplified by PCR (oVPL1219 and oVPL1220), followed LCR (Kok et al. 2014) placing the gVPL1 fragment between the start and stop codon located on the pJP028 backbone. The LCR mixture was precipitated and transformed in L. reuteri VPL1014. Transformants were screened by PCR (oVPL329-oVPL363) to confirm cloning of mIL-22. One positive clone was colony purified, a 1.584 kb amplicon was generated by colony PCR, and the integrity of the construct was confirmed by DNA sequencing (GeneWiz). The resultant strain was named VPL3461. We hereafter refer to pVPL3461 when it concerns the plasmid that encodes codon-optimized mIL-22 (FIG. 2).

The nucleotide sequence of pVPL3461 is represented by SEQ ID NO:25. The nucleotide sequence of the IL-22 promoter (L. reuteri native promoter) in pVPL3461 is represented by SEQ ID NO: 26. The nucleotide sequence encoding the signal peptide (SP) in pVPL3461 is represented by SEQ ID NO:27. The nucleotide sequence encoding IL-22 in pVPL3461 is represented by SEQ ID NO:28. The nucleotide sequence of the inverted repeat (IR) in pVPL3461 is represented by SEQ ID NO:29. The nucleotide sequence of the chloramphenicol marker (Cm) in pVPL3461 is represented by SEQ ID NO:30. The nucleotide sequence of the Phelp promoter in pVPL3461 is represented by SEQ ID NO:31. The nucleotide sequence of the erythromycin marker (Em) in pVPL3461 is represented by SEQ ID NO:32.

Additionally, a construct from the pVPL3461 plasmid comprising the promoter, signal peptide, and mIL-22 coding sequence was excised from pVPL3461 and incorporated in the L. reuteri chromosome using methods known in the art. The resultant strain was named VPL3461chr.

TABLE 4

Codon optimization table for L. reuteri F275.*#
Fields: [sequence of nucleotide triplet] [frequency: per thousand] ([number])

| | | | |
|---|---|---|---|
| UUU 29.5 (16802) | UCU 9.7 (5521) | UAU 24.8 (14106) | UGU 4.4 (2479) |
| UUC 11.3 (6447) | UCC 4.0 (2249) | UAC 12.4 (7068) | UGC 1.5 (861) |
| UUA 36.4 (20706) | UCA 15.0 (8537) | UAA 2.3 (1307) | UGA 0.4 (219) |
| UUG 15.4 (8765) | UCG 4.3 (2458) | UAG 0.7 (374) | UGG 10.8 (6134) |
| CUU 22.1 (12555) | CCU 9.7 (5489) | CAU 15.3 (8708) | CGU 14.1 (7995) |
| CUC 6.3 (3597) | CCC 3.4 (1927) | CAC 8.0 (4562) | CGC 5.9 (3360) |
| CUA 9.4 (5359) | CCA 17.7 (10090) | CAA 35.0 (19877) | CGA 8.6 (4869) |
| CUG 5.3 (3005) | CCG 6.0 (3428) | CAG 11.7 (6653) | CGG 9.9 (5610) |
| AUU 50.7 (28857) | ACU 22.3 (12657) | AAU 36.1 (20541) | AGU 15.6 (8850) |
| AUC 16.7 (9524) | ACC 9.8 (5550) | AAC 15.8 (8968) | AGC 6.7 (3786) |
| AUA 5.8 (3300) | ACA 16.6 (9464) | AAA 36.6 (20829) | AGA 3.3 (1872) |
| AUG 26.9 (15321) | ACG 9.2 (5230) | AAG 30.3 (17232) | AGG 1.4 (792) |
| GUU 35.0 (19884) | GCU 29.0 (16508) | GAU 43.5 (24740) | GGU 24.3 (13830) |
| GUC 9.2 (5210) | GCC 12.4 (7053) | GAC 15.2 (8617) | GGC 10.9 (6178) |
| GUA 16.1 (9176) | GCA 25.3 (14409) | GAA 45.6 (25918) | GGA 19.8 (11244) |
| GUG 7.7 (4354) | GCG 9.8 (5573) | GAG 11.2 (6360) | GGG 10.1 (5771) |

*This table was made based on 568,715 codons among 1,900 CDSs on chromosomal DNA of strain F275.
Coding GC 39.50% 1st letter GC 51.33% 2nd letter GC 35.17% 3rd letter GC 32.00%.

Determine mIL-22 Secretion.

Figure 3A:
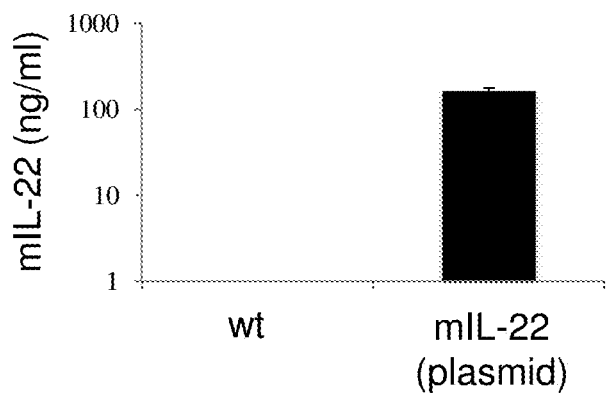
FIGS. 3A and 3B show secretion of mIL-22 from engineered *L. reuteri* cells.

Strains L. reuteri VPL1014 and VPL3461 were cultured in LDM-III as described above, and the supernatants were collected after centrifugation (5 min at 3,214×g), followed by filter-sterilization (0.22 am, Millipore). One hundred microliters of filter-sterilized supernatant from L. reuteri VPL1014 and VPL3461 was assessed for the presence of mIL-22 by ELISA (R&D systems). Production of mIL-22 could not be detected for L. reuteri 6575-VPL (15 pg/ml cut-off limit), while strain VPL3461 secreted mIL-22 at levels of 164.2±13.1 ng/ml (n=3). See FIG. 3A.

Figure 3B:
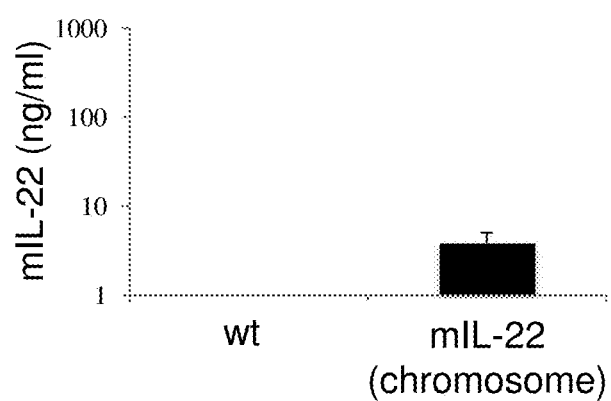

Secretion of mIL-22 from VPL3461chr was similarly tested. VPL3461chr showed detectable mIL-22 secretion. See FIG. 3B.

Plasmid Stability of pVPL3461 in L. reuteri VPL1014.

Prior to assessing biological activity of the L. reuteri-produced mIL-22 in mice, we first assessed the stability of pVPL3461. Normally, selection of plasmids is achieved by supplementation of an antibiotic, but we wanted to avoid the supplementation of antibiotics in mice to maintain a fully competent microbiota. VPL3461 was cultured overnight in LDM-III (supplemented with antibiotics). Cells were washed to remove residual antibiotics, followed by sub-culturing to antibiotic-free LDM-III (OD600=0.1). After 1 passage (20 hr, ~10 generations), we showed that 96% of the cell population was resistant to erythromycin, demonstrating that the rate of loss of pVPL3461 was 0.4% per generation, and would be considered stable enough for in-vivo assessment of biological activity.

Animal Trial.

Figure 4:
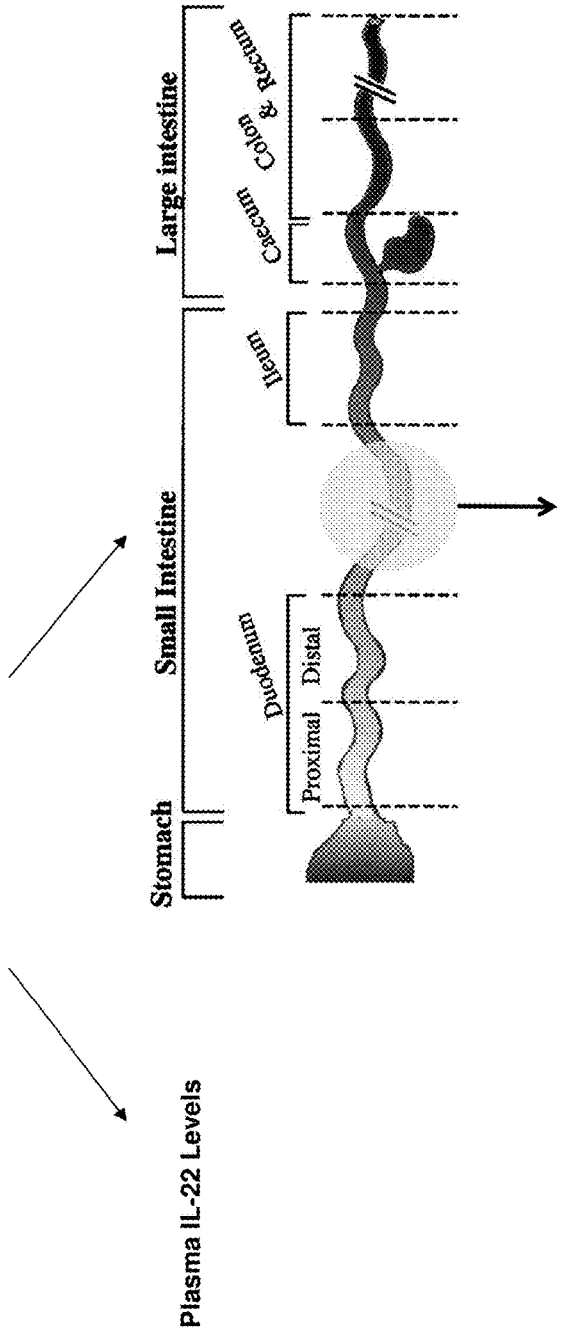
FIG. 4 shows a schema of methods for assessing delivery of mIL-22 to mice from orally administered *L. reuteri* cells harboring the pVPL3461 plasmid, including detecting plasma mIL-22 levels and determining expression of mIL-22 target genes reg3-beta and reg3-gamma.

Twenty-four 6-week old male B6 mice (C57BL/6J) were purchased from Jackson Labs (Bar Harbor, Me.). Animals were housed at an environment-controlled facility with a 12-hour light and dark cycle. Both diet (standard chow, LabDiet, St Louis, Mo.) and water were freely available to the animals. After transport, animals were allowed to adjust to the new environment for two weeks, after which treatment by gavage started. Three groups of 8 animals per group were treated daily for 7 consecutive days. Treatments were sham gavage where the animals were subjected to insertion of a gavaging needle without administering anything (control), gavage of L. reuteri VPL1014 (WT group) and gavage of L. reuteri VPL3461 (LR_mIL-22). Bacterial load administrated was ~1×10$^9$ CFU in a volume of 100 al of the respective bacterial supernatant. See FIG. 4.

Blood collection to assess plasma IL-22 levels.

At T=0 (prior to the start of treatment) and at T=7 (2 hours after the last gavage) of the animal trial, blood was collected (50 al per animal) via retro orbital puncture. Plasma was isolated from whole blood sample by centrifugation at 9,000 rpm for 7 min and the plasma fraction was stored at −80° C. until use. By ELISA (as described above) we determined plasma mIL-22 levels. See FIG. 4.

Figure 5:
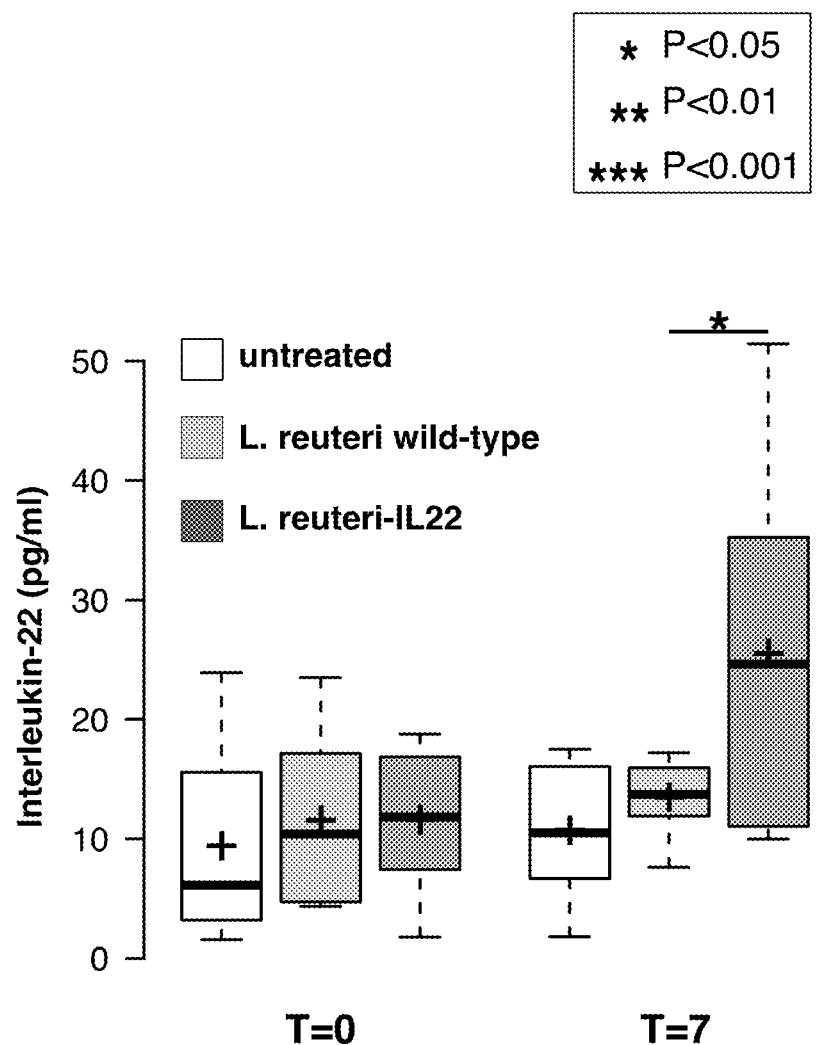
FIG. 5 shows plasma IL-22 levels in sham gavaged mice (untreated), mice gavaged with wild-type *L. reuteri* ($1\times10^9$ CFU), and mice gavaged with *L. reuteri* engineered to secrete IL-22 ($1\times10^9$ CFU). Eight-week-old male C57BL/6 mice (n=8/group) were gavaged daily for 7 days. Blood was collected from the animals prior to gavage treatment (T=0) and one hour after gavage at the 7th day of administration (T=7). Center lines show the median values. Box limits indicate the 25th and 75th percentiles as determined by R software. Whiskers extend 1.5 times the interquartile range from the 25th and 75th percentiles.

Plasma IL-22 levels after 7 days gavage are shown in FIG. 5. The mice administered L. reuteri VPL3461 showed a statistically significant increase in plasma IL-22 levels compared to controls.

Figure 6:
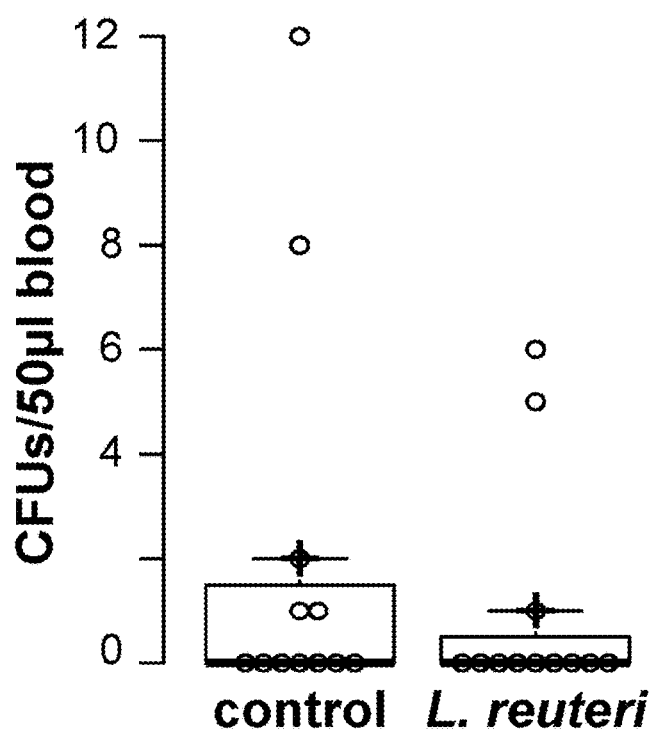
FIG. 6 shows counts of bacteria detected in blood from the same mice described above for FIG. 5.

We also assessed whether the administered L. reuteri VPL1014 and L. reuteri VPL3461 could be detected in the bloodstream of the animals after 7 days gavage. From each animal, 50 µl blood was plated on deMan Rogosa Sharp (MRS) medium that is selective for a broad range of lactic acid bacteria, including L. reuteri. The results are shown in FIG. 6. The prolonged daily administration of L. reuteri did not increase the total number of lactic acid bacteria in the bloodstream. As determined by colony morphology, the bacteria detected in the bloodstream of animals that were gavaged with L. reuteri were not L. reuteri. L. reuteri yields (after 48 h) on MRS plates small-medium sized colonies that are opaque. From the 3 animals in which we detected bacteria in the bloodstream, all colonies were pigmented, mostly yellow, and some were red-ish. Some colonies were also extremely large. The size combined with the pigmented phenotype made it evident that the recovered bacteria in the bloodstream were not L. reuteri.

These results indicate that the systemic increase of IL-22 was not a result of *L. reuteri* VPL3461 itself entering the bloodstream.

cDNA Synthesis.

To assess biological functionality of *L. reuteri* secreted mIL-22, we assess gene expression levels of reg3-beta and reg3-gamma. Both genes are known to be upregulated by IL-22 (Loonen et al. 2013, Sovran et al. 2015). Part of the small intestine (jejunum) of each animal was processed for RNA isolation. First, samples were homogenized (Omni TH, Omni International) followed by RNA isolation and on-column DNaseI treatment (Qiagen), after which an additional DNase treatment was conducted (RQI DNase; Promega, Madison, Wis.). RNA was quantified by Qubit analysis (Invitrogen). One ag RNA was reverse transcribed using the iScript cDNA synthesis kit (Bio-Rad Laboratories, Richmond, Calif.). See FIG. 4.

Quantitative Real-Time PCR.

Relative gene expression levels were determined using the CFX96™ real-time PCR (Bio-Rad). Expression of reg3-beta and reg3-gamma was determined relative to that of the housekeeping gene β-actin. The qRT-PCR was performed with the SYBR Green PCR master mix (Bio-Rad). Primers for amplification of: reg3b (oVPL1313-oVPL1314), reg3g (oVPL1315-oVPL1316), and β-actin (oVPL1325-oVPL1326) are listed in Table 3. Gene expression of the reg genes in the jejunum tissues relative to β-actin was determined by the Relative Expression Software Tool (REST), which allows comparison of gene expression between groups of animals (Pfaffl et al. 2001 and 2002).

Figure 7:
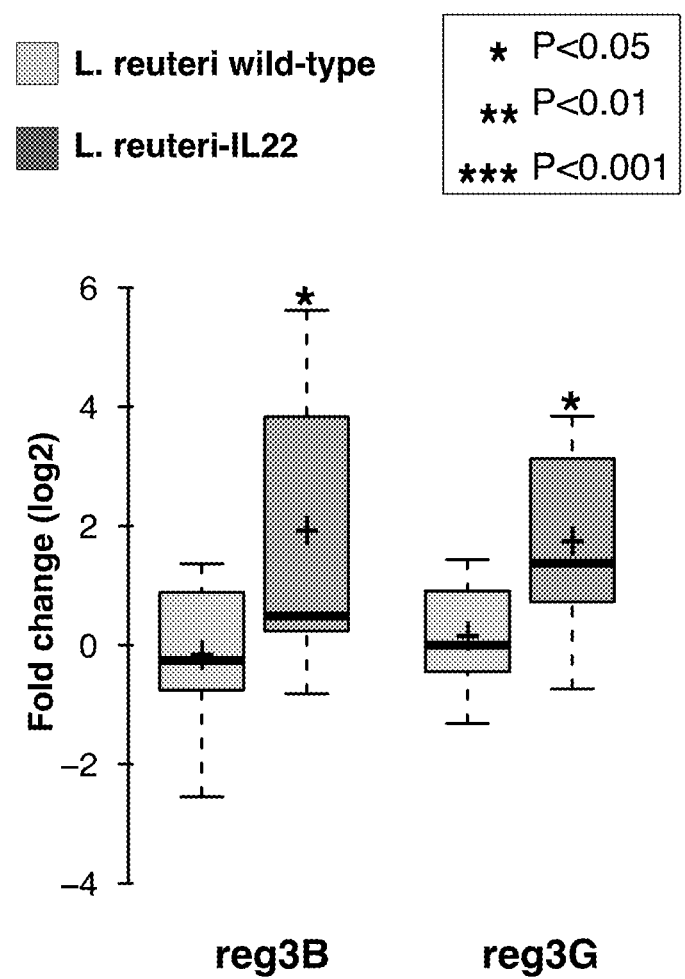
FIG. 7 shows jejunal expression of mIL-22 target genes reg3-beta (reg3B) and reg3-gamma (reg3G) in the same mice described above for FIG. 5. After 7 days gavage, animals were sacrificed, and part of the small intestine (jejunum) was subjected to total RNA isolation followed by cDNA synthesis and real-time PCR. Fold changes and significance are reported based on comparison to the untreated group, and data is normalized against the housekeeping gene 1-actin. Data were analyzed with the REST software package (Pfaffl et al. 2002). Data are presented in a box-whisker plot (see comments above with respect to FIG. 5 for details).

As shown in FIG. 7, mice administered IL-22-expressing *L. reuteri* VPL3461 showed an average of 4.7-fold and 3-fold increased expression of reg3-beta and reg3-gamma, respectively in the jejunum compared to mice administered wild-type *L. reuteri*, demonstrating that the secreted IL-22 is biologically active.

Figure 8:
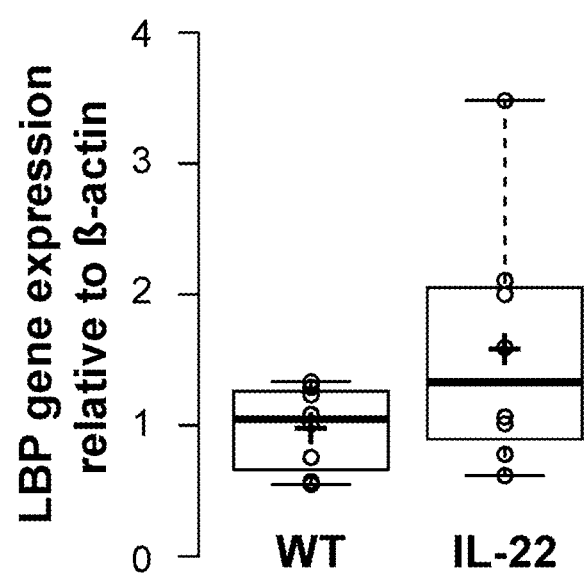
FIG. 8 shows liver expression of lipopolysaccharide-binding protein (LBP) in the same mice described above for FIG. 5.

We also determined liver expression of the gene encoding the lipopolysaccharide-binding protein (LBP), which is known to be regulated by IL-22. Expression levels were relative to that of the control (1-actin). As shown in FIG. 8, liver LBP expression was not changed in animals that received wild-type *L. reuteri*. Animals administered the IL-22-expressing *L. reuteri* VPL3461 displayed an increased level of LBP gene expression, varying from 1.5-fold to 3.5-fold. We did not detect a statistical difference in gene expression, but we predict including more animals per group will show a statistical difference.

Metabolic Syndrome Trial.

IL-22 has been shown to alleviate metabolic disorders and provide other therapeutic effects in diabetic subjects. See Wang et al. 2014. We tested whether administering IL-22-secreting *L. reuteri* to mice with diet-induced obesity could recapitulate these effects.

Thirty-six 6-week old male B6 mice (C57BL/6J) were purchased from Jackson Labs (Bar Harbor, Me.). Animals were housed at an environmental controlled facility with a 12-hour light and dark cycle. After transport, animals were caged (4 mice per cage) and immediately placed on an ad libitum high-fat diet: 45% kcal fat diet containing 21% milk fat and 2% soybean oil (Cat. No. TD08811, Envigo, Indianapolis, Ind.), for eight weeks. Based on prior work, animals placed on this diet for eight weeks develop signs of metabolic syndrome, including glucose intolerance and insulin sensitivity.

After eight weeks on the high-fat diet, we initiated the treatment of daily gavage for a period of seven weeks. Animals in a first group (12 animals) received a sham gavage of 100 µl PBS without bacteria. Animals in a second group (12 animals) received 100 µl of *L. reuteri* VPL1014 ($10^9$ CFU). Animals in a third group (12 animals) received 100 al of the IL-22-secreting *L. reuteri* VPL3461 ($10^9$ CFU).

Figure 9A:
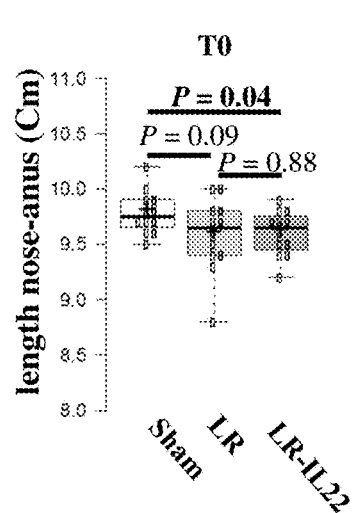
FIGS. 9A-9C show results from length measurements in animals after eight weeks of high-fat diet feeding (T0) and after seven subsequent weeks of treatment (T7) of daily sham gavage of PBS without bacteria (sham), daily gavage of *L. reuteri* VPL1014 (LR), or daily gavage of the IL-22-secreting *L. reuteri* VPL3461 (LR-IL22).
Figure 9B:
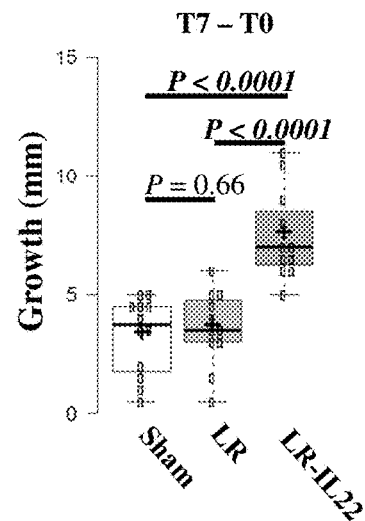

The length (nose to anus) of the animals was determined after eight weeks high-fat diet feeding (T0), and was subsequently determined every week after for seven weeks (T7). Each animal was measured three times and the values were averaged. After eight weeks high-fat diet feeding but prior to the start of the treatment (T0) we observed that the animals assigned to be receiving treatment were similar in length (P=0.88) but both groups were marginally smaller than the control group (control vs WT, P=0.09; control vs recombinant, P=0.04). See FIG. 9A. After seven weeks of treatment (T7) we observed that the animals gavaged with the IL-22-secreting *L. reuteri* grew faster than animals gavaged with *L. reuteri* wild-type (P<0.0001) or PBS control (P<0.0001). See FIG. 9B. The increased growth is purely driven by recombinant IL-22 that is delivered by *L. reuteri* because *L. reuteri* wild-type does not influence growth compared to the PBS control (P=0.66)

Figure 9C:
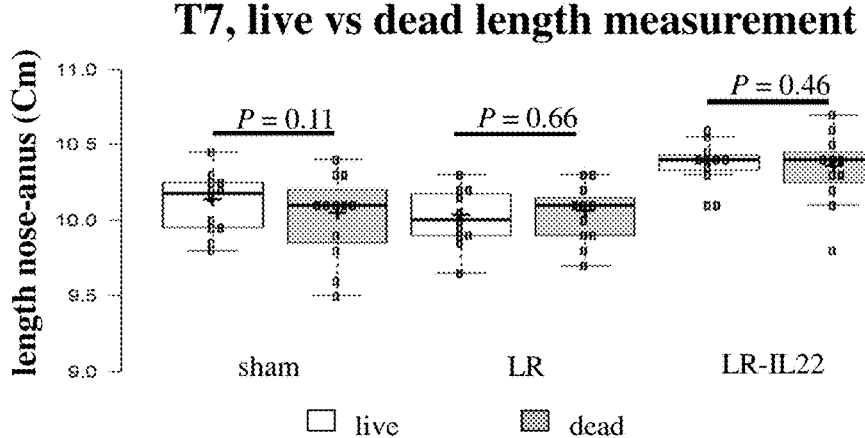

Healthy mice have a natural curve in their spine. When mice are obese, the excess weight will press the spine down. When measuring length of the animal from nose to anus, obese mice may be perceived to be longer. To determine if this would have affected our body length data, we measured animals alive and after euthanasia at T7. When anesthetized or dead, any bias derived from differences in curvature will be lost as the animal is completely relaxed. As shown in FIG. 9C, there is no difference in the body length of the animals when measured alive or dead. This finding conclusively confirmed that recombinant *L. reuteri* secreting IL-22 promotes growth.

Figure 10:
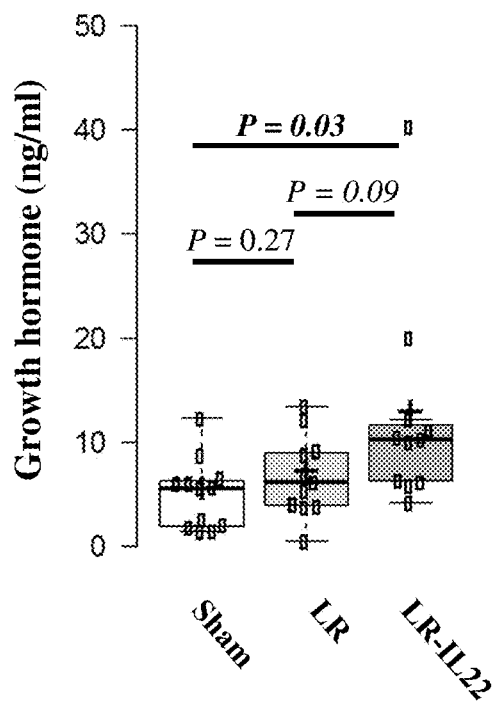
FIG. 10 shows growth hormone levels in the serum of the mice described above for FIGS. 9A-9C at T7.

Our growth data led us to measure growth hormone levels in the serum. As shown in FIG. 10, mice treated with IL-22-secreting *L. reuteri* had increased levels of growth hormone compared to the PBS control (P=0.03) at T7. Levels were also higher in the recombinant group compared to the wild-type but this was not statistically significant (P=0.09).

Figure 11A:
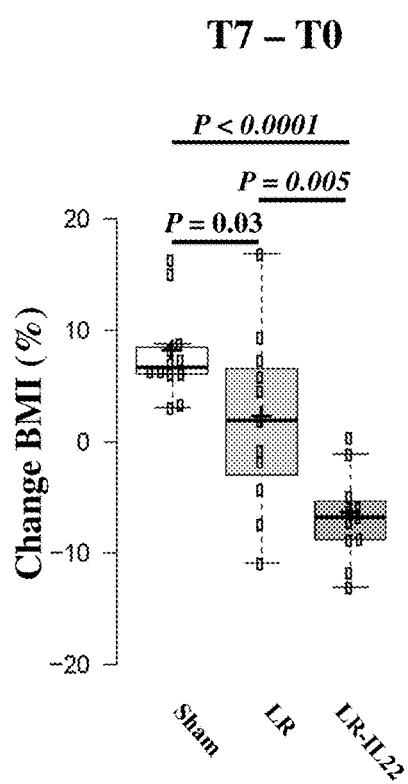
FIGS. 11A and 11B show percentage differences in body mass index (BMI) in the mice described above for FIGS. 9A-9C.
Figure 11B:
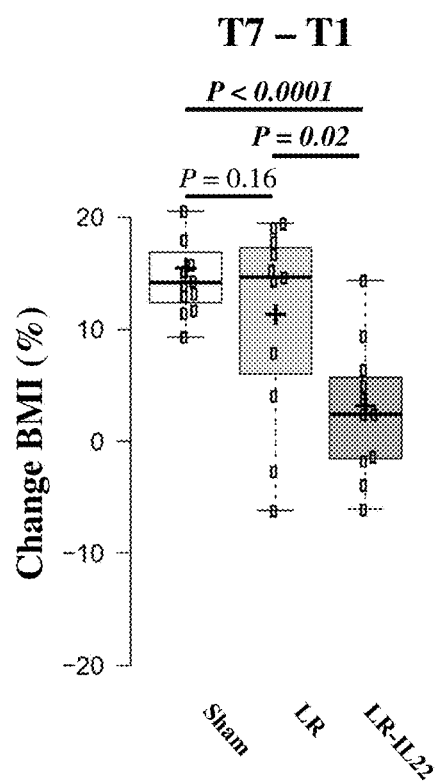

In mice, the body mass index (BMI) can be an indication of metabolic syndrome. We determined the BMI of the mice as follows: (body weight (g)/[nose-anus length $(mm)]^2$). As shown in FIGS. 11A and 11B, *L. reuteri*-derived IL-22 reduces the change in BMI over the course of seven weeks (T7-T0) and six weeks (T7-T1), respectively.

Figure 12A:
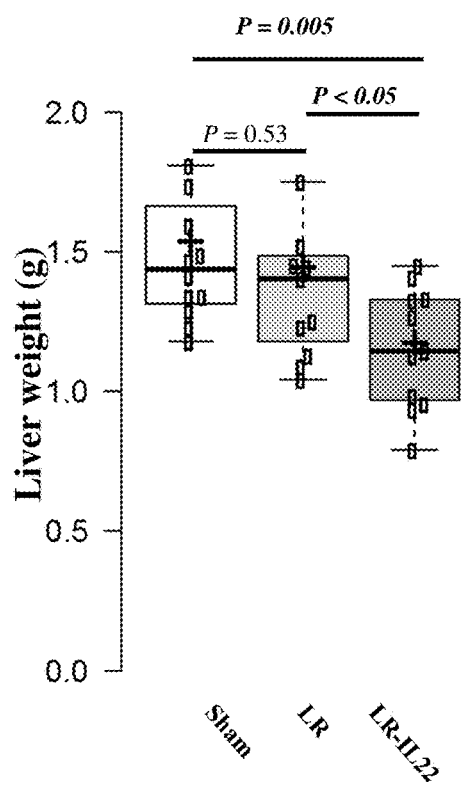
FIGS. 12A and 12B show absolute liver weights and liver weights relative to mouse body weights in the mice described above for FIGS. 9A-9C at T7.
Figure 12B:
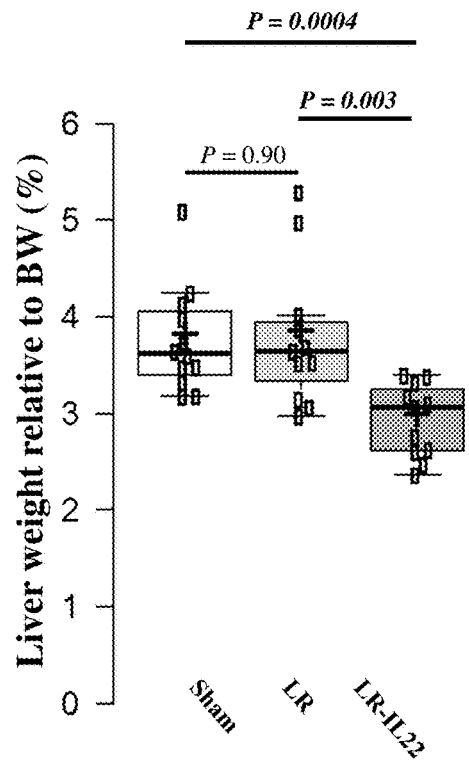

Following seven weeks treatment (T7), animals were killed, tissues were harvested, and liver weights were determined. Liver weights are shown as absolute liver weights (FIG. 12A) or liver weight relative to mouse body weight (FIG. 12B). Both metrics showed that IL-22-secreting *L. reuteri* yielded significantly lower liver weights compared to the wild-type *L. reuteri* or PBS control.

These results show that oral administration of recombinant *L. reuteri* engineered to secrete IL-22 systemically delivers IL-22 in a manner that results in systemic physiological effects. In the present case, the systemic physiological effects included an increase in growth, an increase in growth hormone in the plasma, a reduction in BMI, and a reduction in liver weight. The administration reversed many effects associated with metabolic syndrome. We predict that systemic delivery of IL-22 will also reverse many metabolic symptoms of diabetic subjects, including hyperglycemia and insulin resistance, and will improve insulin sensitivity, preserve gut mucosal barrier and endocrine functions, decrease endotoxemia and chronic inflammation, and reverse the dysregulation of lipid metabolism in liver and adipose tissues.

Delivery of Peptides Other than IL-22.

*L. reuteri* can be used to systemically deliver polypeptides other than IL-22. This can be performed by replacing the mIL-22 reading frame from the pVPL3461 plasmid and replacing it with the reading frame of any polypeptide of interest. The edited plasmid can then be introduced into *L. reuteri* using methods described above, and the *L. reuteri* harboring the edited plasmid can be administered as described above. We predict that the *L. reuteri* so modified will be capable of systemically delivering any polypeptide of interest without the bacterium itself being distributed systemically. We predict that diseases and conditions that are alleviated by systemic administration of such polypeptides will be alleviated with the *L. reuteri*-dependent systemic delivery of the peptides.

Statistical Analysis.

In the present examples, ANOVA (analysis of variance) was used for data analysis, and significance in comparisons between groups was analyzed by t-test. Significant difference was considered when P-value is lower than 0.05.

REFERENCES

Ahrné, S., Molin, G., & Axelsson, L. (1992). Transformation of *Lactobacillus reuteri* with electroporation: Studies on the erythromycin resistance plasmid pLUL631. *Current Microbiology*, 24: 199-205.

Alvarez-Sieiro P, Montalbin-López M, Mu D, Kuipers O P. Bacteriocins of lactic acid bacteria: extending the family. *Appl Microbiol Biotechnol*. 2016. 100(7):2939-51.

Bahey-El-Din M, Gahan C G M, Griffin B T. 2010. *Lactococcus lactis* as a cell factory for delivery of therapeutic proteins. Curr Gene Ther 10:34-45.

Barrangou R, van Pijkeren J P. Exploiting CRISPR-Cas immune systems for genome editing in bacteria. Curr Opin Biotechnol. 2016 February; 37:61-8.

Becker S C, Dong S, Baker J R, Foster-Frey J, Pritchard D G, Donovan D M. 2009. LysK CHAP endopeptidase domain is required for lysis of live staphylococcal cells. FEMS Microbiol Lett 294:52-60.

Beisel C L, Gomaa A A, Barrangou R. 2014. A CRISPR design for next-generation antimicrobials. Genome Biol 15:516.

Bikard D, Euler C W, Jiang W, Nussenzweig P M, Goldberg G W, Duportet X, Fischetti V A, Marraffini L A. 2014. Exploiting CRISPR-Cas nucleases to produce sequence-specific antimicrobials. Nat Biotech 32:1146-1150.

Borysowski J, Weber-Dabrowska B, Górski A. Bacteriophage endolysins as a novel class of antibacterial agents. *Exp Biol Med* (Maywood). 2006 April; 231(4):366-77.

Britton, R. A.; Irwin, R.; Quach, D.; Schaefer, L.; Zhang, J.; Lee, T.; Parameswaran, N.; McCabe, L. R. Probiotic *L. reuteri* Treatment Prevents Bone Loss in a Menopausal Ovariectomized Mouse Model. *J Cell Physiol* 2014, 229 (11), n/a-n/a DOI: 10.1002/jcp.24636.

Chatel J-M, Pothelune L, Ah-Leung S, Corthier G, Wal J-M, Langella P. 2008. In vivo transfer of plasmid from food-grade transiting lactococci to murine epithelial cells. Gene Ther 15:1184-1190.

Cheng X, Zhang X, Pflugrath J W, Studier F W. 1994. The structure of bacteriophage T7 lysozyme, a zinc amidase and an inhibitor of T7 RNA polymerase. Proc Natl Acad Sci USA 91:4034-4038.

Citorik R J, Mimee M, Lu T K. 2014. Sequence-specific antimicrobials using efficiently delivered RNA-guided nucleases. Nat Biotech 32:1141-1145.

Cotter P D, Ross R P, Hill C. 2013. Bacteriocins |[mdash]| a viable alternative to antibiotics?Nat Rev Microbiol 11:95-105.

Cronin, M.; Akin, A. R.; Collins, S. A.; Meganck, J.; Kim, J.-B.; Baban, C. K.; Joyce, S. A.; van Dam, G. M.; Zhang, N.; van Sinderen, D.; et al. High resolution in vivo bioluminescent imaging for the study of bacterial tumour targeting. *PLoS ONE* 2012, 7 (1), e30940 DOI: 10.1371/journal.pone.0030940.

Cronin M, Morrissey D, Rajendran S, El Mashad S M, van Sinderen D, O'Sullivan G C, Tangney M. Orally administered bifidobacteria as vehicles for delivery of agents to systemic tumors. *Mol Ther.* 2010 July; 18(7):1397-407.

de Azevedo M, Karczewski J, Lefevre F, Azevedo V, Miyoshi A, Wells J M, Langella P, Chatel J-M. 2012. In vitro and in vivo characterization of DNA delivery using recombinant *Lactococcus lactis* expressing a mutated form of *L. monocytogenes* Internalin A. BMC Microbiol 12:299.

de Ruyter, P. G.; Kuipers, O. P.; de Vos, W. M. Controlled gene expression systems for *Lactococcus lactis* with the food-grade inducer nisin. *Appl Environ Microbiol* 1996, 62 (10), 3662-3667.

De Weirdt R, Crabbé A, Roos S, Vollenweider S, Lacroix C, van Pijkeren J-P, Britton R A, Sarker S, Van de Wiele T, Nickerson C A. 2012. Glycerol Supplementation Enhances *L. reuteri*'s Protective Effect against *S. Typhimurium* Colonization in a 3-D Model of Colonic Epithelium. *PLoS ONE* 7:e37116.

Dishisha T, Pereyra L P, Pyo S-H, Britton R A, Hatti-Kaul R. 2014. Flux analysis of the *Lactobacillus reuteri* propanediol-utilization pathway for production of 3-hydroxypropionaldehyde, 3-hydroxypropionic acid and 1,3-propanediol from glycerol. Microb Cell Fact 13:76.

Doleyres Y, Beck P, Vollenweider S, Lacroix C. 2005. Production of 3-hydroxypropionaldehyde using a two-step process with *Lactobacillus reuteri*. Appl Microbiol Biotechnol 68:467-474.

Eaton, K. A.; Honkala, A.; Auchtung, T. A.; Britton, R. A. Probiotic *Lactobacillus reuteri* Ameliorates Disease Due to Enterohemorrhagic *Escherichia coli* in Germfree Mice. *Infect Immun* 2011, 79 (1), 185-191 DOI: 10.1128/IAI.00880-10.

Elzagheid, A.; Algars, A.; Bendardaf, R.; Lamlum, H.; Ristamaki, R.; Collan, Y.; Syrjanen, K.; Pyrhonen, S. E-cadherin expression pattern in primary colorectal carcinomas and their metastases reflects disease outcome. *World J Gastroenterol* 2006, 12 (27), 4304-4309.

Feliza A. Bourguet, Brian E. Souza, Angela K. Hinz, Matthew A. Coleman, and Paul J. Jackson. Characterization of a Novel Lytic Protein Encoded by the *Bacillus cereus* E33L Gene ampD as a *Bacillus anthracis* Antimicrobial Protein. *Appl Environ Microbiol.* 2012 April; 78(8): 3025-3027.

Field D, Connor P M O, Cotter P D, Hill C, Ross R P. 2008. The generation of nisin variants with enhanced activity against specific gram-positive pathogens.—PubMed—NCBI. Mol Microbiol 69:218-230.

Field D, Begley M, O'Connor P M, Daly K M, Hugenholtz F, Cotter P D, Hill C, Ross R P. 2012. Bioengineered Nisin A Derivatives with Enhanced Activity against Both Gram Positive and Gram Negative Pathogens. PLoS ONE 7:e46884

Fischetti V A. 2004. The use of phage lytic enzymes to control bacterial infections, p 321-334 In Kutter E, Sulakvelidze A, editors. (ed), Bacteriophages: biology and applications. CRC Press, Boca Raton, Fla.

Fischetti V A. 2009. Bacteriophage Lysins: the Ultimate Enzybiotic Enzybiotics. John Wiley & Sons, Inc., Hoboken, N.J., USA Fogel, M. R.; Gray, G. M. Starch hydrolysis in man: an intraluminal process not requiring membrane digestion. J Appl Physiol 1973, 35 (2), 263-267.

Foster, P. L. Methods for determining spontaneous mutation rates. *Meth Enzymol* 2006, 409, 195-213.

Frese S A, Benson A K, Tannock G W, Loach D M, Kim J, Zhang M, Oh P L, Heng N C, Patil P B, Juge N, Mackenzie D A, Pearson B M, Lapidus A, Dalin E, Tice H, Goltsman E, Land M, Hauser L, Ivanova N, Kyrpides N C, Walter J. The evolution of host specialization in the vertebrate gut symbiont Lactobacillus reuteri. PLoS Genet. 2011 February; 7(2):e1001314.

Gibson D G, Young L, Chuang R-Y, Venter J C, Hutchison C A, Smith H O. 2009. Enzymatic assembly of DNA molecules up to several hundred kilobases. Nat Meth 6:343-345.

Gomaa A A, Klumpe H E, Luo M L, Selle K, Barrangou R, Beisel C L. 2014. Programmable Removal of Bacterial Strains by Use of Genome-Targeting CRISPR-Cas Systems. mBio 5:e00928-13.

Green et al., Molecular Cloning: A Laboratory Manual, 4th ed., Cold Spring Harbor Laboratory Press, 2012.

Guimarães, V. D.; Gabriel, J. E.; Lefevre, F.; Cabanes, D.; Gruss, A.; Cossart, P.; Azevedo, V.; Langella, P. Internalin-expressing Lactococcus lactis is able to invade small intestine of guinea pigs and deliver DNA into mammalian epithelial cells. *Microbes Infect* 2005, 7 (5-6), 836-844 DOI: 10.1016/j.micinf.2005.02.012.

Guimarães V, Innocentin S, Chatel J-M, Lefevre F, Langella P, Azevedo V, 582 Miyoshi A. 2009. A new plasmid vector for DNA delivery using lactococci. Genet Vaccines Ther 7:4.

Huyghebaert N, Vermeire A, Neirynck S, Steidler L, Remaut E, Remon J P. Development of an enteric-coated formulation containing freeze-dried, viable recombinant Lactococcus lactis for the ileal mucosal delivery of human interleukin-10. *Eur J Pharm Biopharm.* 2005 August; 60(3):349-59.

Jacobs C, Huang L J, Bartowsky E, Normark S, Park J T. Bacterial cell wall recycling provides cytosolic muropeptides as effectors for beta-lactamase induction. *EMBO J.* 1994 Oct. 3; 13(19):4684-94.

Jacobs C, Joris B, Jamin M, Klarsov K, Van Beeumen J, Mengin-Lecreulx D, van Heijenoort J, Park J T, Normark S, Fèbre J M. AmpD, essential for both beta-lactamase regulation and cell wall recycling, is a novel cytosolic N-acetylmuramyl-L-alanine amidase. *Mol Microbiol.* 1995 February; 15(3):553-9.

Jensen H, Roos S, Jonsson H, Rud I, Grimmer S, van Pijkeren J P, Britton R A, Axelsson L. Role of Lactobacillus reuteri cell and mucus-binding protein A (CmbA) in adhesion to intestinal epithelial cells and mucus in vitro. *Microbiology.* 2014 April; 160(Pt 4):671-81.

Kok, S. D., Stanton, L. H., Slaby, T., Durot, M., Holmes, V. F., Patel, K. G., Platt, D., Shapland, E. B. and Chandran, S. S. (2014). Rapid and reliable DNA assembly via ligase cycling reaction. *ACS synthetic biology,* 3: 97-106.

Kommineni S, Bretl D J, Lam V, Chakraborty R, Hayward M, Simpson P, Cao Y, Bousounis P, Kristich C J, Salzman N H. 2015. Bacteriocin production augments niche competition by enterococci in the mammalian GI tract. Nature 526:719-722.

Lecuit, M.; Ohayon, H.; Braun, L.; Mengaud, J.; Cossart, P. Internalin of Listeria monocytogenes with an intact leucine-rich repeat region is sufficient to promote internalization. *Infect Immun* 1997, 65 (12), 5309-5319.

Liu, Y.; Fatheree, N. Y.; Mangalat, N.; Rhoads, J. M. Human-derived probiotic Lactobacillus reuteri strains differentially reduce intestinal inflammation. *Am J Physiol Gastrointest Liver Physiol* 2010, 299 (5), G1087-G1096 DOI: 10.1152/ajpgi.00124.2010.

Loessner M J. Bacteriophage endolysins—current state of research and applications. *Curr Opin Microbiol.* 2005 August; 8(4):480-7.

Loessner M J, Kramer K, Ebel F, Scherer S. C-terminal domains of Listeria monocytogenes bacteriophage murein hydrolases determine specific recognition and high-affinity binding to bacterial cell wall carbohydrates. *Mol Microbiol.* 2002 April; 44(2):335-49.

Loonen, L. M., Stolte, E. H., Jaklofsky, M. T., Meijerink, M., Dekker, J., van Baarlen, P., & Wells, J. M. (2014). REG3γ-deficient mice have altered mucus distribution and increased mucosal inflammatory responses to the microbiota and enteric pathogens in the ileum. Mucosal immunology, 7: 939-947.

López R, García E, Garcia P, Garcia J L. The pneumococcal cell wall degrading enzymes: a modular design to create new lysins? Microb Drug Resist. 1997; 3(2):199-211.

Mackenzie D A, Jeffers F, Parker M L, Vibert-Vallet A, Bongaerts R J, Roos S, Walter J, Juge N. Strain-specific diversity of mucus-binding proteins in the adhesion and aggregation properties of Lactobacillus reuteri. *Microbiology.* 2010 November; 156(Pt 11):3368-78. Oh J H, van Pijkeren J P. CRISPR-Cas9-assisted recombineering in Lactobacillus reuteri. Nucleic Acids Res. 2014; 42(17): e131.

Navarre W W, Ton-That H, Faull K F, Schneewind O. 1999. Multiple Enzymatic Activities of the Murein Hydrolase from Staphylococcal Phage φ11. Journal of Biological Chemistry 274:15847-15856.

Nelson D, Schuch R, Chahales P, Zhu S, Fischetti V A. 2006. PlyC: A multimeric bacteriophage lysin. Proc Natl Acad Sci USA 103:10765-10770.

Nicoletti M, Bertani G. 1983. DNA fusion product of phage P2 with plasmid pBR322: A new phasmid. Mol Gen Genet 189:343-347.

Oh, P. L.; Benson, A. K.; Peterson, D. A.; Patil, P. B.; Moriyama, E. N.; Roos, S.; Walter, J. Diversification of the gut symbiont Lactobacillus reuteri as a result of host-driven evolution. *ISME J* 2010, 4 (3), 377-387 DOI: 10.1038/ismej.2009.123.

Oh J H, van Pijkeren J P. CRISPR-Cas9-assisted recombineering in Lactobacillus reuteri.
*Nucleic Acids Res.* 2014; 42(17):e131.

Paez-Espino D, Morovic W, Sun C L, Thomas B C, Ueda K-I, Stahl B, Barrangou R, Banfield J F. 2013. Strong bias in the bacterial CRISPR elements that confer immunity to phage. Nat Comms 4:1430-1430.

Pálffy, R.; Gardlik, R.; Hodosy, J.; Behuliak, M.; Resko, P.; Radvinsky, J.; Celec, P. Bacteria in gene therapy: bactofection versus alternative gene therapy. *Gene Ther* 2006, 13 (2), 101-105 DOI:10.1038/sj.gt.3302635.

Pfaffl, M. W. (2001). A new mathematical model for relative quantification in real-time RT-PCR. *Nucleic acids research,* 29: e45-e45.

Pfaffl, M. W., Horgan, G. W., & Dempfle, L. (2002). Relative expression software tool (REST©) for group-wise comparison and statistical analysis of relative expression results in real-time PCR. Nucleic acids research, 30: e36-e36.

Rajpal G, Liu M, Zhang Y, Arvan P. Single-chain insulins as receptor agonists. *Mol Endocrinol.* 2009 May; 23(5):679-88.

Riboulet-Bisson E, Sturme M H J, Jeffery I B, O'Donnell M M, Neville B A, Forde B M, Claesson M J, Harris H, Gardiner G E, Casey P G, Lawlor P G, O'Toole P W, Ross R P. 2012. Effect of *Lactobacillus salivarius* Bacteriocin Abp118 on the Mouse and Pig Intestinal Microbiota. PLoS ONE 7:e31113.

Riedel, C. U.; Monk, I. R.; Casey, P. G.; Morrissey, D.; O'Sullivan, G. C.; Tangney, M.; Hill, C.; Gahan, C. G. M. Improved luciferase tagging system for *Listeria monocytogenes* allows real-time monitoring in vivo and in vitro. *Appl Environ Microbiol* 2007, 73 (9), 3091-3094 DOI: 10.1128/AEM.02940-06.

Robert S, Steidler L. 2014. Recombinant *Lactococcus lactis* can make the difference in antigen-specific immune tolerance induction, the Type 1 Diabetes case. *Microb Cell Fact* 13:S11.

Rosche, W. A.; Foster, P. L. Determining mutation rates in bacterial populations. Methods 2000, 20 (1), 4-17.

Sabat R, Ouyang W, Wolk K. Therapeutic opportunities of the IL-22-IL-22R1 system. *Nat Rev Drug Discov.* 2014 January; 13(1):21-38.

Schaefer L, Auchtung T A, Hermans K E, Whitehead D, Borhan B, Britton R A. 2010. The antimicrobial compound reuterin (3-hydroxypropionaldehyde) induces oxidative stress via interaction with thiol groups. *Microbiology* 156:1589-1599.

Sheehan M M, Stanley E, Fitzgerald G F, van Sinderen D. 1999. Identification and characterization of a lysis module present in a large proportion of bacteriophages infecting *Streptococcus thermophilus*. Appl Environ Microbiol 65:569-577.

Shi, Y.; Yan, Y.; Ji, W.; Bin Du; Meng, X.; Wang, H.; Sun, J. Characterization and determination of holin protein of *Streptococcus suis* bacteriophage SMP in heterologous host. *Virol J* 2012, 9 (1), 70-70 DOI: 10.1186/1743-422X-9-70.

Singh K, Kadesjö E, Lindroos J, Hjort M, Lundberg M, Espes D, Carlsson P O, Sandler S, Thorvaldson L. Interleukin-35 administration counteracts established murine type 1 diabetes—possible involvement of regulatory T cells. *Sci Rep.* 2015 Jul. 30; 5:12633.

Sovran, B., Loonen, L. M., Lu, P., Hugenholtz, F., Belzer, C., Stolte, E. H., . . . & Dekker, J. (2015). IL-22-STAT3 pathway plays a key role in the maintenance of ileal homeostasis in mice lacking secreted mucus barrier. *Inflammatory bowel diseases*, 21: 531-542.

Spinler J K, Taweechotipatr M, Rognerud C L, Ou C N, Tumwasorn S, Versalovic J. 2008. Human-derived probiotic *Lactobacillus reuteri* demonstrate antimicrobial activities targeting diverse enteric bacterial pathogens. Anaerobe 14:166-171.

Steidler L, Hans W, Schotte L, Neirynck S, Obermeier F, Falk W, Fiers W, Remaut E. Treatment of murine colitis by *Lactococcus lactis* secreting interleukin-10. *Science.* 2000 Aug. 25; 289(5483): 1352-5.

Sulakvelidze, Alexander; Alavidze, Zemphira; and J. Glenn Morris, Jr. Bacteriophage Therapy. *Antimicrob Agents Chemother.* 2001, 45(3): 649-659).

Summers W C. Bacteriophage therapy. *Annu Rev Microbiol.* 2001; 55:437-51.

Sun J, Furio L, Mecheri R, van der Does A M, Lundeberg E, Saveanu L, Chen Y, van Endert P, Agerberth B, Diana J. Pancreatic β-Cells Limit Autoimmune Diabetes via an Immunoregulatory Antimicrobial Peptide Expressed under the Influence of the Gut Microbiota. Immunity. 2015 Aug. 18; 43(2):304-17.

Sznol, M.; Lin, S. L.; Bermudes, D.; Zheng, L.-M.; King, I. Use of preferentially replicating bacteria for the treatment of cancer. *Journal of Clinical Investigation* 2000, 105 (8), 1027-1030 DOI:10.1172/JCI9818.

Talarico T L, Casas I A, Chung T C, Dobrogosz W J. 1988. Production and isolation of reuterin, a growth inhibitor produced by *Lactobacillus reuteri*. Antimicrob Agents Chemother 32:1854-1858.

Tannock, G. W.; Wilson, C. M.; Loach, D.; Cook, G. M.; Eason, J.; O'Toole, P. W.; Holtrop, G.; Lawley, B. Resource partitioning in relation to cohabitation of *Lactobacillus* species in the mouse forestomach. *ISME J* 2011, 6 (5), 927-938 DOI: 10.1038/ismej.2011.161.

Thomas, C. M.; Hong, T.; van Pijkeren, J.P.; Hemarajata, P.; Trinh, D. V.; Hu, W.; Britton, R. A.; Kalkum, M.; Versalovic, J. Histamine Derived from Probiotic *Lactobacillus reuteri* Suppresses TNF via Modulation of PKA and ERK Signaling. *PLoS ONE* 2012, 7 (2), e31951 DOI: 10.1371/journal.pone.0037116.g006.

van Pijkeren, J.P.; Morrissey, D.; Monk, I. R.; Cronin, M.; Rajendran, S.; O'Sullivan, G. C.; Gahan, C. G. M.; Tangney, M. A novel *Listeria monocytogenes*-based DNA delivery system for cancer gene therapy. *Hum. Gene Ther.* 2010, 21 (4), 405-416 DOI: 10.1089/hum.2009.022.

van Pijkeren J P, Britton R A. High efficiency recombineering in lactic acid bacteria. *Nucleic Acids Res.* 2012 May; 40(10):e76.

van Pijkeren, J.P.; Britton, R. A. Precision genome engineering in lactic acid bacteria. *Microb Cell Fact* 2014, 13 Suppl 1, S10-S10 DOI: 10.1186/1475-2859-13-S1-S10.

van Pijkeren J-P, Neoh K M, Sirias D, Findley A S, Britton R A. 2012. Exploring optimization parameters to increase ssDNA recombineering in *Lactococcus lactis* and *Lactobacillus reuteri*. Bioengineered 3:209-217.

Wang I N, Smith D L, Young R. 2000. Holins: the protein clocks of bacteriophage infections. Annual Reviews in Microbiology.

Wang X, Ota N, Manzanillo P, Kates L, Zavala-Solorio J, Eidenschenk C, Zhang J, Lesch J, Lee W P, Ross J, Diehl L, van Bruggen N, Kolumam G, Ouyang W. Interleukin-22 alleviates metabolic disorders and restores mucosal immunity in diabetes. *Nature.* 2014 Oct. 9; 514(7521): 237-41.

Wells M. et al. *Lactococcus lactis*: high-level expression of tetanus toxin fragment C and protection against lethal challenge. *Mol. Microbiol.,* 8 (1993), pp. 1155-1162.

Zhang Y, Eigenbrot C, Zhou L, Shia S, Li W, Quan C, Tom J, Moran P, Di Lello P, Skelton N J, Kong-Beltran M, Peterson A, Kirchhofer D. Identification of a small peptide that inhibits PCSK9 protein binding to the low density lipoprotein receptor. *J Biol Chem.* 2014 Jan. 10; 289(2):942-55.

Zhou, Y; Liang, Y; Lynch, K. H.; Dennis, J. J.; Wishart, D. S. PHAST: A Fast Phage Search Tool. 2011, 39 (suppl), W347-W352 DOI: 10.1093/nar/gkr485.

We claim:

1. A method of systemically introducing a polypeptide into a bloodstream of a subject, the method comprising administering into the gastrointestinal tract of the subject a bacterium that produces and releases the polypeptide, wherein the bacterium comprises a recombinant gene configured to express the polypeptide, wherein the bacterium is administered in an amount effective to introduce the polypeptide in the bloodstream of the subject in a detectable amount without the bacterium being introduced in the bloodstream of the subject in a detectable amount, wherein the bacterium is *Lactobacillus reuteri*.

2. The method of claim 1, wherein the bacterium is administered in an amount effective to introduce the polypeptide in the bloodstream in an amount effective to induce at least one direct systemic effect in the subject.

3. The method of claim 1, wherein the bacterium is administered in an amount effective to introduce the polypeptide in the bloodstream in an amount effective to induce at least one direct effect in a non-gastrointestinal tissue in the subject.

4. The method of claim 1, wherein the bacterium is administered in an amount effective to introduce the polypeptide in the bloodstream in an amount effective to induce at least one direct effect in a tissue selected from the group consisting of liver, muscles, lungs, kidneys, pancreas, and adipose tissue in the subject.

5. The method of claim 1, wherein the subject suffers from a condition treatable with systemic introduction of the polypeptide and wherein the polypeptide is introduced in the bloodstream of the subject in an amount effective to treat the condition.

6. The method of claim 1, wherein the subject suffers from a condition treatable with systemic introduction of the polypeptide but not treatable with local introduction of the polypeptide to the gastrointestinal tract without systemic introduction of the polypeptide, and wherein the polypeptide is introduced in the bloodstream of the subject in an amount effective to treat the condition.

7. The method of claim 1, wherein the polypeptide is selected from the group consisting of a cytokine, a hormone, an antibody, an antimicrobial peptide, and an antigenic peptide.

8. The method of claim 1, wherein the polypeptide is selected from the group consisting of interleukin-22 (IL-22), interleukin-35 (IL-35), insulin, leptin, cathelicidin related antimicrobial peptide, a peptide inhibitor of proprotein convertase subtilisin/kexin type 9 (PCSK9), and an endolysin.

9. The method of claim 8, wherein the subject suffers from at least one condition selected from the group consisting of insulin resistance, hyperglycemia, lipid dysregulation, hyperlipidemia, and obesity, and wherein the polypeptide is introduced in the bloodstream of the subject in an amount effective to treat the at least one condition.

10. The method of claim 1, wherein the polypeptide is interleukin-22 (IL-22).

11. The method of claim 1, wherein the polypeptide is a cytokine.

* * * * *

SEQUENCE LISTING

<160> NUMBER OF SEQ ID NOS: 32

<210> SEQ ID NO 1
<211> LENGTH: 311
<212> TYPE: DNA
<213> ORGANISM: Lactobacillus reuteri

<400> SEQUENCE: 1

```
taccaagaat aactttcatc gtaaaaggca agtaattgag gaaacttgaa gtttttctct     60
attacttgcc ttctttattt tattaagcta aatatgtttt aaataattaa ctataacgga    120
cctgcttggc ggaaactaaa cagtaagaac tttaaattat aaaaatctgc aaccgttttc    180
taaaattttg cgcaagcggt tgcgcaaaat ttttaaattt gatattatta atattgcaat    240
aattcatgaa gcgcttacaa taatcacaag tgtcttttag aactatttta taagttaagg    300
agttgttagc a                                                         311
```

<210> SEQ ID NO 2
<211> LENGTH: 146
<212> TYPE: PRT
<213> ORGANISM: Homo sapiens

<400> SEQUENCE: 2

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile
145

<210> SEQ ID NO 3
<211> LENGTH: 209
<212> TYPE: PRT
<213> ORGANISM: Artificial Sequence
<220> FEATURE:
<223> OTHER INFORMATION: Recombinant IL-35

<400> SEQUENCE: 3

Arg Lys Gly Pro Pro Ala Ala Leu Thr Leu Pro Arg Val Gln Cys Arg
1               5                   10                  15

Ala Ser Arg Tyr Pro Ile Ala Val Asp Cys Ser Trp Thr Leu Pro Pro
            20                  25                  30

Ala Pro Asn Ser Thr Ser Pro Val Ser Phe Ile Ala Thr Tyr Arg Leu
        35                  40                  45

```
Gly Met Ala Ala Arg Gly His Ser Trp Pro Cys Leu Gln Gln Thr Pro
    50                  55                  60

Thr Ser Thr Ser Cys Thr Ile Thr Asp Val Gln Leu Phe Ser Met Ala
 65              70                  75                  80

Pro Tyr Val Leu Asn Val Thr Ala Val His Pro Trp Gly Ser Ser
                 85                  90                  95

Ser Phe Val Pro Phe Ile Thr Glu His Ile Ile Lys Pro Asp Pro
                100             105             110

Glu Gly Val Arg Leu Ser Pro Leu Ala Glu Arg Gln Leu Gln Val Gln
            115                 120                 125

Trp Glu Pro Pro Gly Ser Trp Pro Phe Pro Glu Ile Phe Ser Leu Lys
130                 135                 140

Tyr Trp Ile Arg Tyr Lys Arg Gln Gly Ala Ala Arg Phe His Arg Val
145                 150                 155                 160

Gly Pro Ile Glu Ala Thr Ser Phe Ile Leu Arg Ala Val Arg Pro Arg
                165                 170                 175

Ala Arg Tyr Tyr Val Gln Val Ala Ala Gln Asp Leu Thr Asp Tyr Gly
                180                 185                 190

Glu Leu Ser Asp Trp Ser Leu Pro Ala Thr Ala Thr Met Ser Leu Gly
            195                 200                 205

Lys

<210> SEQ ID NO 4
<211> LENGTH: 9
<212> TYPE: PRT
<213> ORGANISM: Artificial Sequence
<220> FEATURE:
<223> OTHER INFORMATION: Peptide Linker

<400> SEQUENCE: 4

Gln Arg Gly Gly Gly Gly Gln Arg
 1               5

<210> SEQ ID NO 5
<211> LENGTH: 146
<212> TYPE: PRT
<213> ORGANISM: Homo sapiens

<400> SEQUENCE: 5

Val Pro Ile Gln Lys Val Gln Asp Asp Thr Lys Thr Leu Ile Lys Thr
 1               5                  10                  15

Ile Val Thr Arg Ile Asn Asp Ile Ser His Thr Gln Ser Val Ser Ser
                 20                  25                  30

Lys Gln Lys Val Thr Gly Leu Asp Phe Ile Pro Gly Leu His Pro Ile
             35                  40                  45

Leu Thr Leu Ser Lys Met Asp Gln Thr Leu Ala Val Tyr Gln Gln Ile
     50                  55                  60

Leu Thr Ser Met Pro Ser Arg Asn Val Ile Gln Ile Ser Asn Asp Leu
 65                  70                  75                  80

Glu Asn Leu Arg Asp Leu Leu His Val Leu Ala Phe Ser Lys Ser Cys
                 85                  90                  95

His Leu Pro Trp Ala Ser Gly Leu Glu Thr Leu Asp Ser Leu Gly Gly
                100                 105                 110

Val Leu Glu Ala Ser Gly Tyr Ser Thr Glu Val Val Ala Leu Ser Arg
            115                 120                 125

Leu Gln Gly Ser Leu Gln Asp Met Leu Trp Gln Leu Asp Leu Ser Pro
130                 135                 140
```

Gly Cys
145

<210> SEQ ID NO 6
<211> LENGTH: 39
<212> TYPE: PRT
<213> ORGANISM: Homo sapiens

<400> SEQUENCE: 6

Phe Ala Leu Leu Gly Asp Phe Phe Arg Lys Ser Lys Glu Lys Ile Gly
1               5                   10                  15

Lys Glu Phe Lys Arg Ile Val Gln Arg Ile Lys Asp Phe Leu Arg Asn
            20                  25                  30

Leu Val Pro Arg Thr Glu Ser
        35

<210> SEQ ID NO 7
<211> LENGTH: 13
<212> TYPE: PRT
<213> ORGANISM: Artificial Sequence
<220> FEATURE:
<223> OTHER INFORMATION: Peptide PCSK9 Inhibitor

<400> SEQUENCE: 7

Thr Val Phe Thr Ser Trp Glu Glu Tyr Leu Asp Trp Val
1               5                   10

<210> SEQ ID NO 8
<211> LENGTH: 30
<212> TYPE: DNA
<213> ORGANISM: Artificial Sequence
<220> FEATURE:
<223> OTHER INFORMATION: Primer oVPL329

<400> SEQUENCE: 8
attccttgga cttcatttac tgggtttaac                                        30

<210> SEQ ID NO 9
<211> LENGTH: 25
<212> TYPE: DNA
<213> ORGANISM: Artificial Sequence
<220> FEATURE:
<223> OTHER INFORMATION: Primer oVPL363

<400> SEQUENCE: 9
taatatgaga taatgccgac tgtac                                             25

<210> SEQ ID NO 10
<211> LENGTH: 50
<212> TYPE: DNA
<213> ORGANISM: Artificial Sequence
<220> FEATURE:
<223> OTHER INFORMATION: Primer oVPL1219

<400> SEQUENCE: 10
ttcatgggga tgaatgcttc tgctaataca ttaccagtta atactcgttg                   50

<210> SEQ ID NO 11
<211> LENGTH: 52
<212> TYPE: DNA
<213> ORGANISM: Artificial Sequence
<220> FEATURE:
<223> OTHER INFORMATION: Primer oVPL1220

<400> SEQUENCE: 11
cttggttttc taattttggt tcaaagatca aacacaagca ttacgtaaac tc          52

<210> SEQ ID NO 12
<211> LENGTH: 26
<212> TYPE: DNA
<213> ORGANISM: Artificial Sequence
<220> FEATURE:
<223> OTHER INFORMATION: Primer oVPL1221

<400> SEQUENCE: 12
gcttgaaacg ttcaattgaa atggca                                       26

<210> SEQ ID NO 13
<211> LENGTH: 24
<212> TYPE: DNA
<213> ORGANISM: Artificial Sequence
<220> FEATURE:
<223> OTHER INFORMATION: Primer oVPL1222

<400> SEQUENCE: 13
tgtaaaacca ataaggactg aagc                                         24

<210> SEQ ID NO 14
<211> LENGTH: 60
<212> TYPE: DNA
<213> ORGANISM: Artificial Sequence
<220> FEATURE:
<223> OTHER INFORMATION: Primer oVPL1223

<400> SEQUENCE: 14
ggagttgctt cagtccttat tggttttaca ttcatgggga tgaatgcttc tgctaataca  60

<210> SEQ ID NO 15
<211> LENGTH: 60
<212> TYPE: DNA
<213> ORGANISM: Artificial Sequence
<220> FEATURE:
<223> OTHER INFORMATION: Primer oVPL1224

<400> SEQUENCE: 15
tgatctttga accaaaatta gaaaaccaag gcttgaaacg ttcaattgaa atggcaatta  60

<210> SEQ ID NO 16
<211> LENGTH: 23
<212> TYPE: DNA
<213> ORGANISM: Artificial Sequence
<220> FEATURE:
<223> OTHER INFORMATION: Primer oVPL1313

<400> SEQUENCE: 16
actccctgaa gaatataccc tcc                                          23

<210> SEQ ID NO 17
<211> LENGTH: 22
<212> TYPE: DNA
<213> ORGANISM: Artificial Sequence
<220> FEATURE:
<223> OTHER INFORMATION: Primer oVPL1314

<400> SEQUENCE: 17
cgctattgag cacagatacg ag                                           22

<210> SEQ ID NO 18
<211> LENGTH: 22
<212> TYPE: DNA

```
<213> ORGANISM: Artificial Sequence
<220> FEATURE:
<223> OTHER INFORMATION: Primer oVPL1315

<400> SEQUENCE: 18
atgcttcccc gtataaccat ca                                             22

<210> SEQ ID NO 19
<211> LENGTH: 22
<212> TYPE: DNA
<213> ORGANISM: Artificial Sequence
<220> FEATURE:
<223> OTHER INFORMATION: Primer oVPL1316

<400> SEQUENCE: 19
ggccatatct gcatcatacc ag                                             22

<210> SEQ ID NO 20
<211> LENGTH: 19
<212> TYPE: DNA
<213> ORGANISM: Artificial Sequence
<220> FEATURE:
<223> OTHER INFORMATION: Primer oVPL1321

<400> SEQUENCE: 20
gatcaccgac aagggcctg                                                 19

<210> SEQ ID NO 21
<211> LENGTH: 21
<212> TYPE: DNA
<213> ORGANISM: Artificial Sequence
<220> FEATURE:
<223> OTHER INFORMATION: Primer oVPL1322

<400> SEQUENCE: 21
ggctatgaaa ctcgtactgc c                                              21

<210> SEQ ID NO 22
<211> LENGTH: 20
<212> TYPE: DNA
<213> ORGANISM: Artificial Sequence
<220> FEATURE:
<223> OTHER INFORMATION: Primer oVPL1325

<400> SEQUENCE: 22
ggctgtattc ccctccatcg                                                20

<210> SEQ ID NO 23
<211> LENGTH: 22
<212> TYPE: DNA
<213> ORGANISM: Artificial Sequence
<220> FEATURE:
<223> OTHER INFORMATION: Primer oVPL1326

<400> SEQUENCE: 23
ccagttggta acaatgccat gt                                             22

<210> SEQ ID NO 24
<211> LENGTH: 500
<212> TYPE: DNA
<213> ORGANISM: Artificial Sequence
<220> FEATURE:
<223> OTHER INFORMATION: gVPL1 Codon-Optimized  IL-22 Coding Sequence

<400> SEQUENCE: 24
attcatgggg atgaatgctt ctgctaatac attaccagtt aatactcgtt gtaaattaga    60
```

```
agttagtaat tttcaacaac catatattgt taatcgtact tttatgttag ctaaagaagc    120
tagtttagct gataataata ctgatgttcg tttaattggt gaaaaattat ttcgtggtgt    180
tagtgctaaa gatcaatgtt atttaatgaa acaagtttta aattttactt tagaagatgt    240
tttattacca caaagtgatc gttttcaacc atatatgcaa gaagttgttc cattttaac     300 taaattaagt aatcaattaa gtagttgtca tattagtggt gatgatcaaa atattcaaaa    360
aaatgttcgt cgtttaaaag aaactgttaa aaaattaggt gaaagtggtg aaattaaagc    420
tattggtgaa ttagatttat tatttatgag tttacgtaat gcttgtgttt gatctttgaa    480
ccaaaattag aaaaccaagg                                                500
```

<210> SEQ ID NO 25
<211> LENGTH: 5090
<212> TYPE: DNA
<213> ORGANISM: Artificial Sequence
<220> FEATURE:
<223> OTHER INFORMATION: Vector pVPL3461

<400> SEQUENCE: 25

```
aatgattgaa aacaaaattg actttaatga aaaaagaaat ttgatgattt catcggttat     60
tttagtaatt gggattggaa atgcctatct tcaattagga aaatatcaat tctctggatt    120
agctgttgca gctgtcctcg ggataataat gaatttaatc cttccacaaa aagccaaaag    180
tgaaatgtag tttgaatttt taagcagagt aagaaaaggc atccgacctc ttactctgct    240
tttttcgtat gataacaaaa caaaaaatta gaggtcgtg  gaaaaaacag attgtaagaa    300
aaagtttatc aagtctaaga aaacgttttc tttacactct tatcaattga ttagtaggta    360
tatataaacc taattttttt tgaattttaa cgaaattaat gatatattaa cattcgtaac    420
ttggggtagt tcgtttattt tgcaacgttc atccaattta caagccaaat tattgttata    480
aggaaagagg tggaatatga atgttatcga agaataatcg aaaggaacaa ttccggaaac    540
aagagccgaa aaagcaacgt tttgcaatta aaaagctcac tgtcggagtt gcttcagtcc    600
ttattggttt tacattcatg gggatgaatg cttctgctaa tacattacca gttaatactc    660
gttgtaaatt agaagttagt aattttcaac aaccatatat tgttaatcgt acttttatgt    720
tagctaaaga agctagtttta gctgataata atactgatgt tcgtttaatt ggtgaaaaat    780
tatttcgtgg tgttagtgct aaagatcaat gttatttaat gaaacaagtt ttaaattta     840 ctttagaaga tgtttttatta ccacaaagtg atcgttttca accatatatg caagaagttg    900
ttccattttt aactaaatta gtaatcaat taagtagttg tcatattagt ggtgatgatc     960
aaaatattca aaaaaatgtt cgtcgtttaa aagaaactgt taaaaaatta ggtgaaagtg   1020
gtgaaattaa agctattggt gaattagatt tattatttat gagtttacgt aatgcttgtg   1080
tttgatcttt gaaccaaaat tagaaaacca aggcttctgc taatacattg aaacgttcaa   1140
ttgaaatggc aattaaacaa attacagcac gtgttgcttt gattgatagc caaaagcag    1200 cagttgataa agcaattact gatattgctg aaaaattgta atttataaat aaaaatcacc   1260
ttttagaggt ggttttttta tttataaatt attcgtttga tttcgctttc gatagaacaa   1320
tcaaagcgag attataaaag ccagtcatta ggcctatctg acaattcctg aatagagttc   1380
ataaacaatc cagcatgata accatcacaa acagaatgat gtacctgtaa agatagcggt   1440
aaatatattg aattaccttt attaatgaat tttcctgctg taataatggg tagaaggtaa   1500
ttactattat tattgatatt taagttaaac ccagtaaatg aagtccaagg aataatagaa   1560
```

```
agagaaaaag catttttcagg tataggtgtt ttgggaaaca atttccccga accattatat    1620
ttctctacat cagaaaggta taaatcataa aactctttga agtcattctt tacaggagtc    1680
caaataccag agaatgtttt agatacacca tcaaaaattg tataaagtgg ctctaactta    1740
tcccaataac ctaactctcc gtcgctattg taaccagttc taaaagctgt atttgagttt    1800
atcacccttg tcactaagaa aataaatgca gggtaaaatt tatatccttc ttgttttatg    1860
tttcggtata aaacactaat atcaatttct gtggttatac taaaagtcgt ttgttggttc    1920
aaataatgat taaatatctc ttttctcttc caattgtcta aatcaatttt attaaagttc    1980
atgggtttca ctctccttct acattttta acctaataat gccaaatacc gtttgccacc    2040
cctctctttt gataattata atattggcga aattcgcttc taaagatgaa acgcaatatt    2100
atatgcttgc tttataattg tgagcgctca caatttatgt gattatacca gcccctcac    2160
tacatgtcaa gaataaactg ccaaagcata atgtaaggaa gataaatccc ataagggcgg    2220
gagcagaatg tccgagacta atgtaaattt gtccaccaat taaaggaccg ataacgcgag    2280
cttctcgagt gcatattttc ggcaatcttc tcaatgagat gctcttcagc atgttcaatg    2340
atgtcgattt tttattaaaa cgtctcaaaa tcgtttctga gacgttttag cgtttatttc    2400
gtttagttat cggcataatc gttaaaacag gcgttatcgt agcgtaaaag cccttgagcg    2460
tagcgtgctt tgcagcgaag atgttgtctg ttagattatg aaagccgatg actgaatgaa    2520
ataataagcg cagcgtcctt ctatttcggt tggaggaggc tcaagggagt ttgagggaat    2580
gaaattccct catgggtttg attttaaaaa ttgcttgcaa ttttgccgag cggtagcgct    2640
ggaaaatttt tgaaaaaaat ttggaatttg gaaaaaaatg ggggaaagg aagcgaattt    2700
tgcttccgta ctacgacccc ccattaagtg ccgagtgcca atttttgtgc caaaaacgct    2760
ctatcccaac tggctcaagg gtttgagggg tttttcaatc gccaacgaat cgccaacgtt    2820
ttcgccaacg tttttttataa atctatatt aagtagcttt attgttgttt ttatgattac    2880
aaagtgatac actaatttta taaaattatt tgattggagt tttttaaatg gtgatttcag    2940
aatcgaaaaa aagagttatg atttctctga caaagagca agataaaaaa ttaacagata    3000
tggcgaaaca aaaaggtttt tcaaaatctg cggttgcggc gttagctata gaagaatatg    3060
caagaaagga atcagaacaa aaaaaataag cgaaagctcg cgttttttaga aggatacgag    3120
ttttcgctac ttgtttttga taaggtaata tatcatggct attaaaaata ctaaagctag    3180
aaatttttgga tttttattat atcctgactc aattcctaat gattggaaag aaaaattaga    3240
gagtttgggc gtatctatgg ctgtcagtcc tttacacgat atggacgaaa aaaaagataa    3300
agatacatgg aatagtagtg atgttatacg aaatggaaag cactataaaa aaccacacta    3360
tcacgttata tatattgcac gaaatcctgt aacaatagaa agcgttagga acaagattaa    3420
gcgaaaattg gggaatagtt cagttgctca tgttgagata cttgattata tcaaaggttc    3480
atatgaatat ttgactcatg aatcaaagga cgctattgct aagaataaac atatatacga    3540
caaaaaagat attttgaaca ttaatgattt tgatattgac cgctatataa cacttgatga    3600
aagccaaaaa agagaattga agaatttact tttagatata gtggatgact ataatttggt    3660
aaatacaaaa gatttaatgg ctttattccg cctaggggga gcggagtttg gaattttaaa    3720
tacgaatgat gtaaaagata ttgtttcaac aaactctagc gcctttagat tatggtttga    3780
gggcaattat cagtgtggat atagagcaag ttatgcaaag gttcttgatg ctgaaacggg    3840
ggaaataaaa tgacaaacaa agaaaaagag ttatttgctg aaaatgagga attaaaaaaa    3900
gaaattaagg acttaaaaga gcgtattgaa agatacagag aaatggaagt tgaattaagt    3960
```

```
acaacaatag atttattgag aggagggatt attgaataaa taaaagccccc cctgacgaaa    4020 gtcgacggca atagttaccc ttattatcaa gataagaaag aaaaggattt ttcgctacgc    4080
tcaaatcctt taaaaaaaca caaaagacca cattttttaa tgtggtcttt attcttcaac    4140
taaagcaccc attagttcaa caaacgaaaa ttggataaag tgggatattt ttaaaatata    4200
tatttatgtt acagtaatat tgactttaa aaaaggattg attctaatga agaaagcaga    4260
caagtaagcc tcctaaattc actttagata aaaatttagg aggcatatca aatgaacgag    4320
aaaaatataa aacacagtca aaactttatt acttcaaaac ataatataga taaaataatg    4380
acaaatataa gattaaatga acatgataat atctttgaaa tcggctcagg aaaaggccat    4440 tttaccccttg aattagtaaa gaggtgtaat ttcgtaactg ccattgaaat agaccataaa    4500
ttatgcaaaa ctacagaaaa taaacttgtt gatcacgata atttccaagt tttaaacaag    4560
gatatattgc agtttaaatt tcctaaaaac caatcctata aaatatatgg taatatacct    4620
tataacataa gtacggatat aatacgcaaa attgttttg atagtatagc taatgagatt    4680
tatttaatcg tggaatacgg gtttgctaaa agattattaa atacaaaacg ctcattggca    4740
ttacttttaa tggcagaagt tgatatttct atattaagta tggttccaag agaatatttt    4800
catcctaaac ctaaagtgaa tagctcactt atcagattaa gtagaaaaaa atcaagaata    4860
tcacacaaag ataaacaaaa gtataattat ttcgttatga aatgggttaa caaagaatac    4920
aagaaaatat ttacaaaaaa tcaatttaac aattccttaa aacatgcagg aattgacgat    4980
ttaaacaata ttagctttga acaattctta tctcttttca atagctataa attatttaat    5040
aagtaataat atgagataat gccgactgta cttttttacag tcggttttct             5090

<210> SEQ ID NO 26
<211> LENGTH: 500
<212> TYPE: DNA
<213> ORGANISM: Lactobacillus reuteri

<400> SEQUENCE: 26
aatgattgaa aacaaaattg actttaatga aaaagaaat ttgatgattt catcggttat     60
tttagtaatt gggattggaa atgcctatct tcaattagga aaatatcaat tctctggatt    120
agctgttgca gctgtcctcg ggataataat gaatttaatc cttccacaaa agccaaaag    180 tgaaatgtag tttgaatttt taagcagagt aagaaaggc atccgacctc ttactctgct    240
tttttcgtat gataacaaaa caaaaaatta agaggtcgtg gaaaaaacag attgtaagaa    300
aaagtttatc aagtctaaga aaacgttttc tttacactct tatcaattga ttagtaggta    360
tatataaacc taattttttt tgaattttaa cgaaattaat gatatattaa cattcgtaac    420
ttggggtagt tcgtttttatt tgcaacgttc atccaattta caagccaaat tattgttata    480
aggaaagagg tggaatatga                                               500

<210> SEQ ID NO 27
<211> LENGTH: 144
<212> TYPE: DNA
<213> ORGANISM: Artificial Sequence
<220> FEATURE:
<223> OTHER INFORMATION: Artificical signal peptide in pVPL3461

<400> SEQUENCE: 27
atgttatcga agaataatcg aaaggaacaa ttccggaaac aagagccgaa aaagcaacgt     60
tttgcaatta aaaagctcac tgtcggagtt gcttcagtcc ttattggttt tacattcatg    120
```

```
gggatgaatg cttctgctaa taca                                          144

<210> SEQ ID NO 28
<211> LENGTH: 438
<212> TYPE: DNA
<213> ORGANISM: Mus musculus

<400> SEQUENCE: 28
ttaccagtta atactcgttg taaattagaa gttagtaatt ttcaacaacc atatattgtt    60
aatcgtactt ttatgttagc taaagaagct agtttagctg ataataatac tgatgttcgt   120
ttaattggtg aaaaattatt tcgtggtgtt agtgctaaag atcaatgtta tttaatgaaa   180
caagttttaa attttacttt agaagatgtt ttattaccac aaagtgatcg ttttcaacca   240
tatatgcaag aagttgttcc attttttaact aaattaagta atcaattaag tagttgtcat   300
attagtggtg atgatcaaaa tattcaaaaa aatgttcgtc gtttaaaaga aactgttaaa   360
aaattaggtg aaagtggtga aattaaagct attggtgaat tagatttatt atttatgagt   420
ttacgtaatg cttgtgtt                                                 438

<210> SEQ ID NO 29
<211> LENGTH: 70
<212> TYPE: DNA
<213> ORGANISM: Artificial Sequence
<220> FEATURE:
<223> OTHER INFORMATION: Inverted repeat in pVPL3461

<400> SEQUENCE: 29
aaaaattgta atttataaat aaaaatcacc ttttagaggt ggttttttta tttataaatt    60
attcgtttga                                                           70

<210> SEQ ID NO 30
<211> LENGTH: 648
<212> TYPE: DNA
<213> ORGANISM: Artificial Sequence
<220> FEATURE:
<223> OTHER INFORMATION: Chloramphenicol marker in pVPL3461

<400> SEQUENCE: 30
atgaacttta ataaaattga tttagacaat tggaagagaa aagagatatt taatcattat    60
ttgaaccaac aaacgacttt tagtataacc acagaaattg atattagtgt tttataccga   120
aacataaaac aagaaggata taaattttac cctgcattta ttttcttagt gacaagggtg   180
ataaactcaa atacagcttt tagaactggt tacaatagcg acggagagtt aggttattgg   240
gataagttag agccactttta taattttttt gatggtgtat ctaaaacatt ctctggtatt   300
tggactcctg taaagaatga cttcaaagag tttatgatt tatacctttc tgatgtagag    360
aaatataatg gttcggggaa attgtttccc aaaacaccta tacctgaaaa tgcttttttct   420 ctttctatta ttccttggac ttcatttact gggtttaact taaatatcaa taataatagt   480
aattaccttc tacccattat tacagcagga aaattcatta taaaggtaa ttcaatatat    540 ttaccgctat ctttacaggt acatcattct gtttgtgatg gttatcatgc tggattgttt   600
atgaactcta ttcaggaatt gtcagatagg cctaatgact ggctttta               648

<210> SEQ ID NO 31
<211> LENGTH: 211
<212> TYPE: DNA
<213> ORGANISM: Artificial Sequence
<220> FEATURE:
<223> OTHER INFORMATION: Phelp promoter in pVPL3461
```

```
<400> SEQUENCE: 31
cattatgctt tggcagttta ttcttgacat gtagtgaggg ggctggtata atcacataaa        60
ttgtgagcgc tcacaattat aaagcaagca tataatattg cgtttcatct ttagaagcga       120
atttcgccaa tattataatt atcaaaagag aggggtggca aacggtattt ggcattatta       180
ggttaaaaaa tgtagaagga gagtgaaacc c                                      211

<210> SEQ ID NO 32
<211> LENGTH: 735
<212> TYPE: DNA
<213> ORGANISM: Artificial Sequence
<220> FEATURE:
<223> OTHER INFORMATION: Erythromycin marker in pVPL3461

<400> SEQUENCE: 32
atgaacgaga aaatataaa acacagtcaa aactttatta cttcaaaaca taatatagat        60
aaaataatga caaatataag attaaatgaa catgataata tctttgaaat cggctcagga       120
aaaggccatt ttacccttga attagtaaag aggtgtaatt tcgtaactgc cattgaaata       180
gaccataaat tatgcaaaac tacagaaaat aaacttgttg atcacgataa tttccaagtt       240
ttaaacaagg atatattgca gtttaaattt cctaaaaacc aatcctataa aatatatggt       300
aatataccct ataacataag tacggatata atacgcaaaa ttgttttttga tagtatagct       360 aatgagattt atttaatcgt ggaatacggg tttgctaaaa gattattaaa tacaaaacgc       420
tcattggcat tactttttaat ggcagaagtt gatatttcta tattaagtat ggttccaaga       480
gaatattttc atcctaaacc taaagtgaat agctcactta tcagattaag tagaaaaaaa       540
tcaagaatat cacacaaaga taaacaaaag tataattatt tcgttatgaa atgggttaac       600
aaagaataca agaaaatatt tacaaaaaat caatttaaca attccttaaa acatgcagga       660
attgacgatt taaacaatat tagctttgaa caattcttat ctcttttcaa tagctataaa       720
ttatttaata agtaa                                                       735
```